United States Patent
Gannoe et al.

(10) Patent No.: US 6,773,440 B2
(45) Date of Patent: Aug. 10, 2004

(54) METHOD AND DEVICE FOR USE IN TISSUE APPROXIMATION AND FIXATION

(75) Inventors: Jamy Gannoe, Redwood City, CA (US); Gary Weller, Los Gatos, CA (US); Craig Gerbi, Mountain View, CA (US); Douglas S. Sutton, Pacifica, CA (US); Gilbert Mata, Jr., Tracy, CA (US); J. Stephen Scott, St. Charles, MO (US)

(73) Assignee: Satiety, Inc., Palo Alto, CA (US)

( * ) Notice: Subject to any disclaimer, the term of this patent is extended or adjusted under 35 U.S.C. 154(b) by 0 days.

(21) Appl. No.: 10/188,547

(22) Filed: Jul. 2, 2002

(65) Prior Publication Data

US 2004/0006351 A1 Jan. 8, 2004

(51) Int. Cl.[7] .......................... A61B 17/08; A61B 17/10
(52) U.S. Cl. ........................................ 606/142; 606/157
(58) Field of Search ................................ 606/153, 213, 606/215, 216; 600/37

(56) References Cited

U.S. PATENT DOCUMENTS

| | | | |
|---|---|---|---|
| 3,870,048 A | * | 3/1975 | Yoon ........................... 606/141 |
| 4,134,405 A | | 1/1979 | Smit |
| 4,315,509 A | | 2/1982 | Smit |
| 4,343,066 A | | 8/1982 | Lance |
| 4,458,681 A | | 7/1984 | Hopkins |
| 4,547,192 A | | 10/1985 | Brodsky et al. |
| 4,558,699 A | | 12/1985 | Bashour |
| 4,610,383 A | | 9/1986 | Rothfuss et al. |
| 4,716,900 A | | 1/1988 | Ravo et al. |
| 4,790,294 A | | 12/1988 | Allred, III et al. |
| 4,841,888 A | | 6/1989 | Mills et al. |
| 5,037,021 A | | 8/1991 | Mills et al. |
| 5,080,663 A | | 1/1992 | Mills et al. |
| 5,250,058 A | | 10/1993 | Miller et al. |
| 5,263,629 A | | 11/1993 | Trumbull et al. |
| 5,327,914 A | | 7/1994 | Shlain |
| 5,330,503 A | | 7/1994 | Yoon |
| 5,345,949 A | | 9/1994 | Shlain |
| 5,376,095 A | | 12/1994 | Ortiz |
| 5,382,231 A | | 1/1995 | Shlain |
| 5,403,326 A | | 4/1995 | Harrison et al. |
| 5,437,291 A | | 8/1995 | Pasricha et al. |

(List continued on next page.)

FOREIGN PATENT DOCUMENTS

| | | |
|---|---|---|
| WO | WO 99/17662 | 4/1999 |
| WO | WO 00/32137 | 6/2000 |
| WO | WO 00/78227 | 12/2000 |
| WO | WO 00/78229 | 12/2000 |
| WO | WO 03/007796 | 1/2003 |

OTHER PUBLICATIONS

Wullstein, C. and Gross, E. (Aug. 2000) "Compression anastomosis (AKA-2) in colorectal surgery: results in 442 consecutive patients" *British Journal of Surgery* 87(8):1071–1075.

Primary Examiner—Michael J. Milano
Assistant Examiner—Paul Roberts
(74) Attorney, Agent, or Firm—Morrison & Foerster LLP

(57) ABSTRACT

Methods and devices for use in tissue approximation and fixation are described herein. The present invention provides, in part, methods and devices for acquiring tissue folds from the anterior and posterior portions of a hollow body organ, e.g., a stomach, positioning the tissue folds for affixing within a fixation zone of the stomach, preferably to create a pouch or partition below the esophagus, and fastening the tissue folds such that a tissue bridge forms excluding the pouch from the greater stomach cavity. The present invention further provides devices for performing a transoral, endoscopic hollow organ division, including a tissue acquisition device capable of acquiring the desired tissue, a tensioning device for positioning the acquired tissue, and a fastening element to secure the outer layers of the acquired tissue such that the desired healing response is achieved.

15 Claims, 28 Drawing Sheets

U.S. PATENT DOCUMENTS

| | | |
|---|---|---|
| 5,452,837 A | 9/1995 | Williamson, IV et al. |
| 5,549,621 A | 8/1996 | Bessler et al. |
| 5,571,116 A | 11/1996 | Bolanos et al. |
| 5,582,616 A | 12/1996 | Bolduc et al. |
| 5,624,381 A | 4/1997 | Kieturakis |
| 5,626,588 A | 5/1997 | Sauer et al. |
| 5,651,769 A | 7/1997 | Waxman et al. |
| 5,676,674 A | 10/1997 | Bolanos et al. |
| 5,690,656 A | 11/1997 | Cope et al. |
| 5,697,943 A | 12/1997 | Sauer et al. |
| 5,728,178 A | 3/1998 | Buffington et al. |
| 5,749,893 A | 5/1998 | Vidal et al. |
| 5,788,715 A | 8/1998 | Watson, Jr. et al. |
| 5,810,882 A | 9/1998 | Bolduc et al. |
| 5,824,008 A | 10/1998 | Bolduc et al. |
| 5,827,298 A | 10/1998 | Hart et al. |
| 5,868,141 A | 2/1999 | Ellias |
| 5,897,534 A | 4/1999 | Heim et al. |
| 5,897,562 A | 4/1999 | Bolanos et al. |
| 5,947,983 A | 9/1999 | Solar et al. |
| 5,964,772 A | 10/1999 | Bolduc et al. |
| 5,964,782 A | 10/1999 | Lafontaine et al. |
| 5,976,161 A | 11/1999 | Kirsch et al. |
| 6,042,538 A | 3/2000 | Puskas |
| 6,067,991 A | 5/2000 | Forsell |
| 6,113,609 A | 9/2000 | Adams |
| 6,136,009 A * | 10/2000 | Mears .................. 606/140 |
| 6,159,146 A | 12/2000 | El Gazayerli |
| 6,179,195 B1 | 1/2001 | Adams et al. |
| 6,197,022 B1 | 3/2001 | Baker |
| 6,231,561 B1 | 5/2001 | Frazier et al. |
| 6,302,917 B1 | 10/2001 | Dua et al. |
| 6,494,888 B1 | 12/2002 | Laufer et al. |
| 6,506,196 B1 | 1/2003 | Laufer |
| 2002/0040226 A1 | 4/2002 | Laufer et al. |
| 2002/0193816 A1 | 12/2002 | Laufer et al. |
| 2003/0065340 A1 * | 4/2003 | Geitz .................. 606/151 |

* cited by examiner

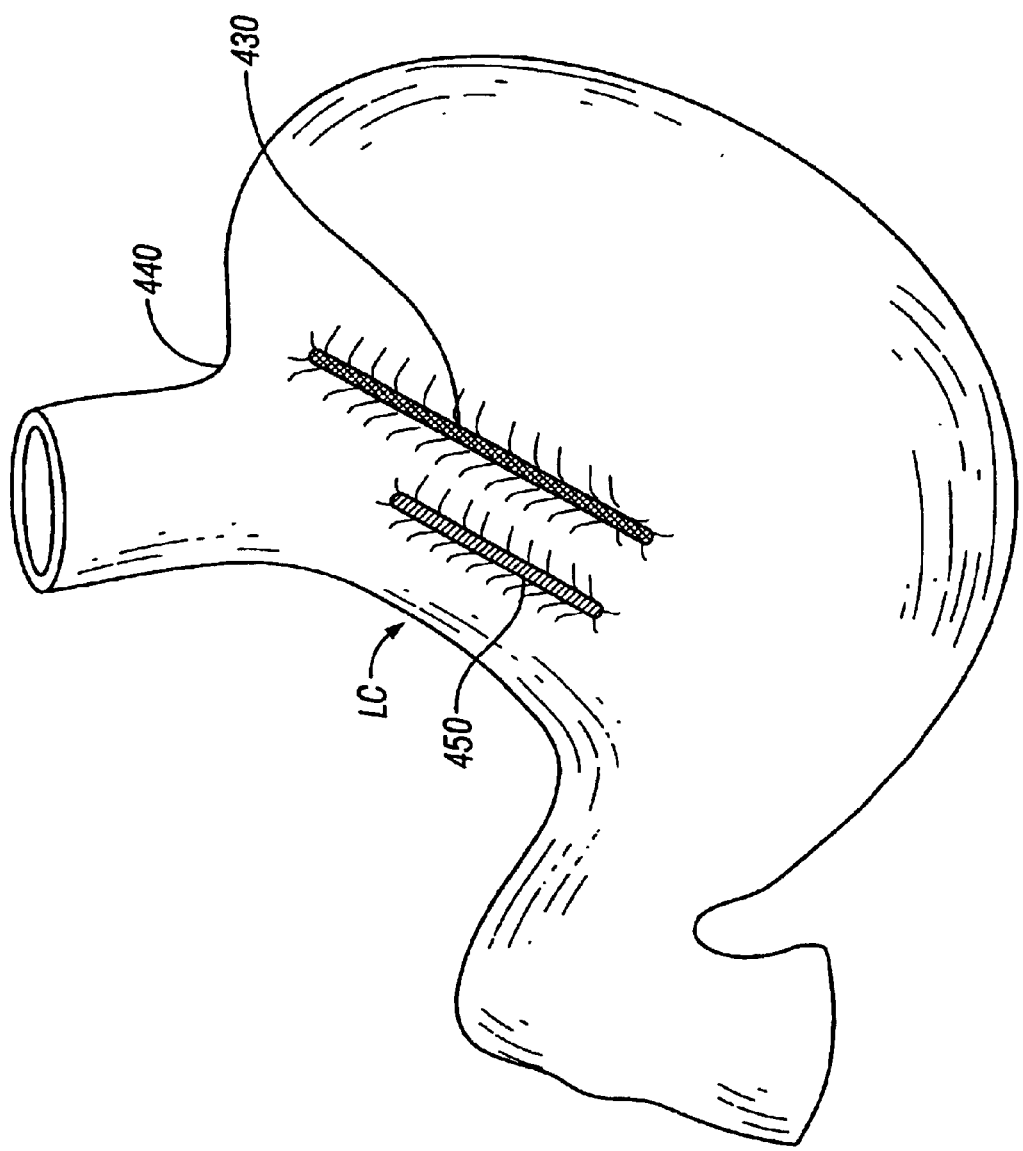

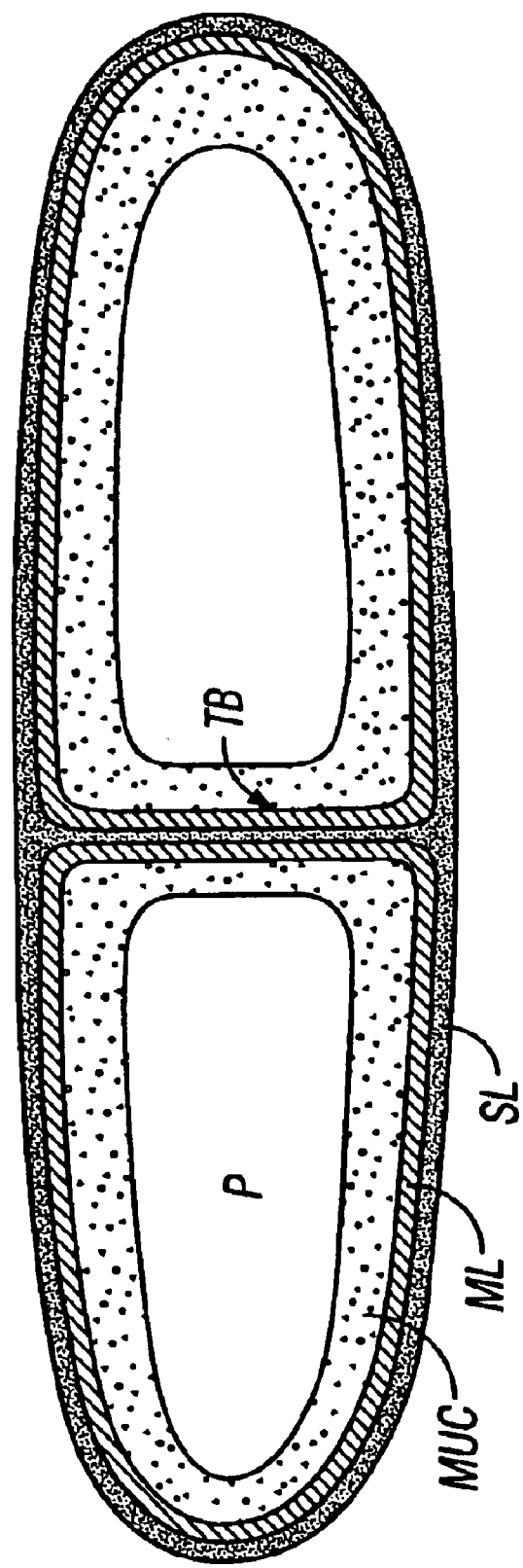

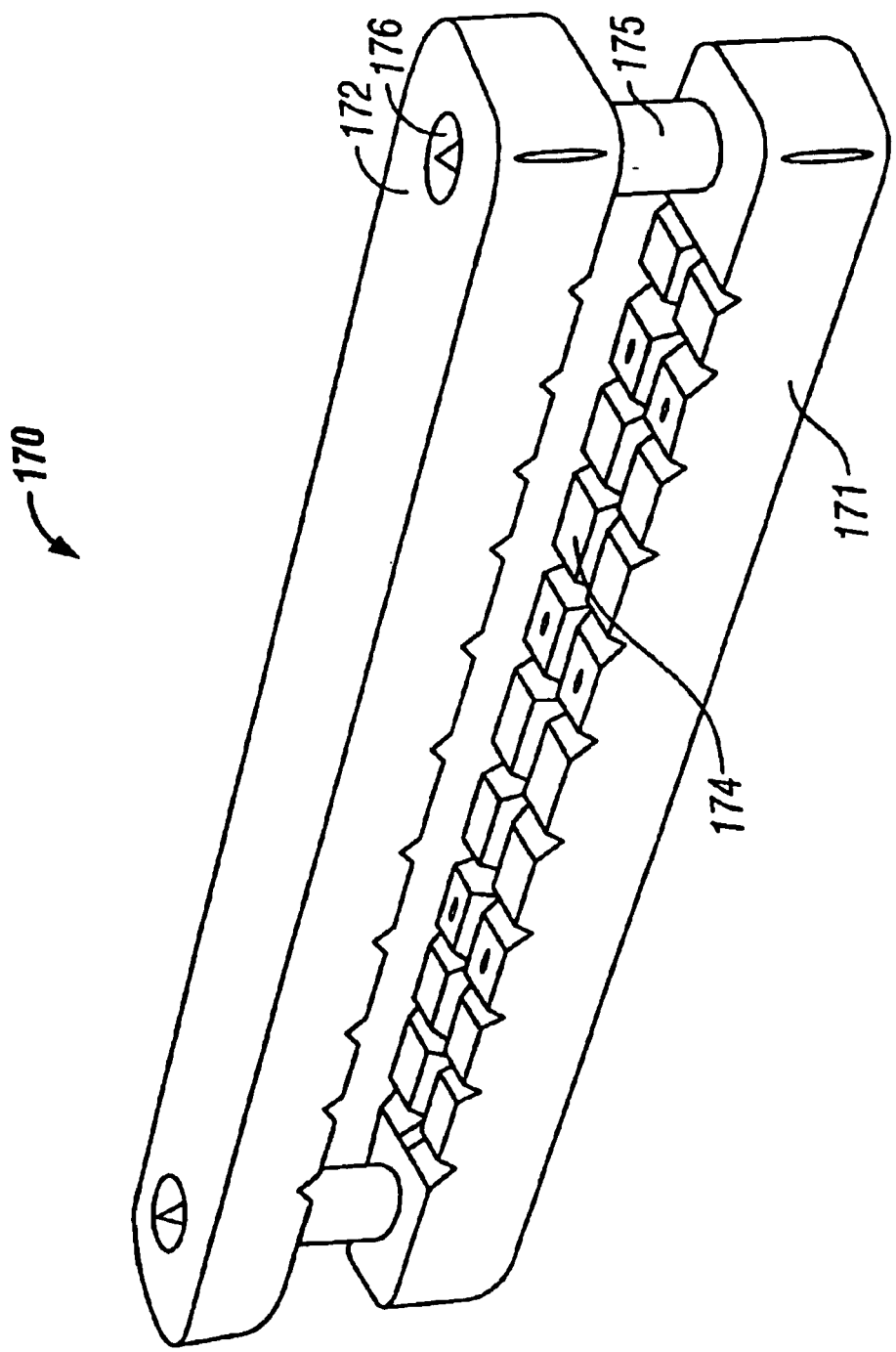

METHOD AND DEVICE FOR USE IN TISSUE APPROXIMATION AND FIXATION

FIELD OF THE INVENTION

The present invention relates generally to medical apparatus and methods and more particularly to devices and methods for dividing a hollow body organ or otherwise restricting or partitioning a certain section of that organ, particularly a stomach, intestine or gastrointestinal tract for purposes of reducing the volume of the hollow body organ. In addition, such tools and techniques may be used to exclude specified tissue sections within a hollow body organ either to reduce volume, or to exclude the portion of tissue that is clinically undesirable, such as in the case of gastroesophogeal reflux disease (GERD) or exclusion of certain sections of the stomach relating to the nuero hormonal pathways for hunger. These devices may be used alone or in conjunction with each other and may be permanently implanted, or removed once they have served their purpose, e.g., the desired tissue effect has occurred (healing), or the clinical benefit has been achieved, for example, the patient has lost the directed or desired amount of weight, or the patient is no longer experiencing reflux.

BACKGROUND OF THE INVENTION

In cases of severe obesity, patients may currently undergo several types of surgery either to tie off or staple portions of the large or small intestine or stomach, and/or to bypass portions of the same to reduce the amount of food desired by the patient, and the amount absorbed by the gastrointestinal tract. The procedures currently available include laparoscopic banding, where a device is used to "tie off" or constrict a portion of the stomach, vertical banded gastroplasty (VBG), or a more invasive surgical procedure known as a Roux-En-Y gastric bypass to effect permanent surgical reduction of the stomach's volume and subsequent bypass of the intestine.

Typically, these stomach reduction procedures are performed surgically through an open incision and staples or sutures are applied externally to the stomach or hollow body organ. Such procedures can also be performed laparoscopically, through the use of smaller incisions, or ports, through trocars and other specialized devices. In the case of laparoscopic banding, an adjustable band is placed around the proximal section of the stomach reaching from the lesser curve (LC) of the stomach around to the greater curve (GC), thereby creating a constriction or "waist" in a vertical manner between the esophagus (ES) and the pylorus (PY) (See Prior Art FIG. 1). During a VBG (See Prior Art FIG. 2) a small pouch (P) (approximately 20 cc in volume) is constructed by forming a vertical partition from the gastroesophageal junction (GEJ) to midway down the lesser curvature of the stomach by externally applying staples, and optionally dividing or resecting a portion of the stomach, followed by creation of a stoma (ST) at the outlet of the partition to prevent dilation of the outlet channel and restrict intake. In a Roux-En-Y gastric bypass (see Prior Art FIG. 3), the stomach is surgically divided into a smaller upper pouch connected to the esophageal inflow, and a lower portion, detached from the upper pouch but still connected to the intestinal tract for purposes of secreting digestive juices. A resected portion of the small intestine is then anastomosed using an end-to-side anastomosis to the upper pouch, thereby bypassing the majority of the intestine and reducing absorption of caloric intake and causing rapid "dumping" of highly caloric or "junk foods".

Although the outcome of these stomach reduction surgeries leads to patient weight loss because patients are physically forced to eat less due to the reduced size of their stomach, several limitations exist due to the invasiveness of the procedures, including time, general anesthesia, healing of the incisions and other complications attendant to major surgery. In addition, these procedures are only available to a small segment of the obese population (morbid obesity, Body Mass Index $\geq 40$) due to their complications, leaving patients who are considered obese or moderately obese with few, if any, interventional options.

In addition to surgical procedures, certain tools exist for approximating or otherwise securing tissue such as the stapling devices used in the above-described surgical procedures and others such as in the treatment of gastroesophogeal reflux (GERD). These devices include the GIA® device (Gastrointestinal Anastomosis device manufactured by Ethicon Endosurgery, Inc. and a similar product by USSC), and certain clamping and stapling devices as described in U.S. Pat. Nos. 5,897,562 and 5,571,116 and 5,676,674, Non-Invasive Apparatus for Treatment of Gastroesophageal Reflux Disease (Bolanos, et al) and U.S. Pat. No. 5,403,326 Method for Performing a Gastric Wrap of the Esophagus for Use in the Treatment of Esophageal Reflux (Harrison et al) for methods and devices for fundoplication of the stomach to the esophagus for treatment of gastro esophageal reflux (GERD). In addition, certain tools as described in U.S. Pat. No. 5,788,715 Telescoping Serial Elastic Band Ligator (Watson et al), U.S. Pat. No. 5,947,983 Tissue Cutting and Stitching Device and Method (Solar et al) detail an endoscopic suturing device that is inserted through an endoscope and placed at the site where the esophagus and the stomach meet. Vacuum is then applied to acquire the adjacent tissue, and a series of stitches are placed to create a pleat in the sphincter to reduce the backflow of acid from the stomach up through the esophagus. These devices can also be used transorally for the endoscopic treatment of esophageal varices (dilated blood vessels within the wall of the esophagus).

Further, certain devices are employed to approximate tissue such as in bowel anastomosis, via traditional suturing or stapling, or employing tools such as the commercially available Valtrac (Devis & Geck Company) and the AKA 2 (see British Journal of Surgery, Vol 87, Iss 8, Page 1071, August 2000), which are circular clamping devices used to affect "compression anastomosis" (e.g. once sufficient clamping force is applied, tissue of the bowel heals together and the device is no longer essential to the joining of the tissue). See also U.S. Pat. No. 5,250,058 Absorbable Anastomotic Fastener Means (Miller et al) and U.S. Pat. No. 5,697,943 Apparatus and Method for Performing Compressional Anastomosis(Sauer et al) and PCT Publication No. WO 99/17662 Anastomosis Ring Insertion Device (Phillips et al).

There is a need for improved devices and procedures. In addition, because of the invasiveness of most of the surgeries used to treat obesity, and the limited success of others, there remains a need for improved devices and methods for more effective, less invasive hollow organ restriction procedures.

SUMMARY OF THE INVENTION

The present invention provides for improved methods and apparatus for the transoral, or endoscopic, division of a hollow body organ, such as the creation of a small stomach pouch. In the case of the present invention, the surgeon or endoscopist may insert devices as described below through the patient's mouth, down the esophagus and into the stomach or intestine as appropriate. The procedure can be performed entirely from within the patient's stomach or other organ, and does not require any external incision. The end result of the procedure is the formation of a variety of organ divisions or plications that serve as barriers or "partitions" or "pouches" that are substantially sealed off from the majority of the organ cavity. For example, in the case of dividing the stomach, the "pouch" or partitions that are created may seal a small portion of the stomach just below the esophagus to allow only small amounts of food or liquid to be consumed by the patient. This pouch or partition will mimic the section of stomach sealed off from the majority of the organ in a traditional obesity surgery heretofore described; however, it can be formed and secured entirely from inside the stomach endoscopically, obviating the need for a prolonged procedure, external incisions, and in some cases, general anesthesia.

The methods and tools of the present invention may also be used in treating GERD in that stomach folds just below the esophagus can be acquired and fastened to create a desired "pleat", thereby effectively extending the length of the esophagus and preventing reflux. A single fold of tissue, or a dual fold of tissue can be acquired. Further, features of the present invention would assist in the longevity of the GE Junction (GEJ)/Esophageal pleat as compared to current devices and techniques as the plication would include a more significant amount of muscular tissue. In addition, the devices and methods of the present invention may be used to revise or repair failures seen in current surgical procedures, such as dilation of the pouch and/or stoma (stomata) formed in a traditional Roux-En-Y gastric bypass, or VBG. In these cases, when the stoma dilates or shifts, the tools of the present invention would be useful to apply pleats at the site of dilation to narrow it, thereby making the stoma functional again, or by further reducing the volume of an existing pouch which has dilated.

The devices shown and described herein can be used to form a pouch or partition by the approximation and fixation of two folds of organ tissue, one fold created in the anterior wall of the organ, and one fold created in the posterior wall of the organ using a tissue acquisition device inserted minimally invasively or transorally into the target organ, e.g., the stomach. A calibration balloon on the end of the tissue acquisition device may also be employed to size the pouch or partition and to position the tools correctly to determine where the folds will be created. Alternatively, the tissue acquisition device may be adapted to receive a standard endoscope to allow viewing of the target region at various points during the procedure.

The devices shown and described herein can also create the tissue folds using vacuum to acquire tissue from both walls using an endoscopic tissue acquisition device having windows or openings spaced apart from each other, preferably 180 degrees from one another. Once the tissue folds are acquired, an optional mechanical retraction/tensioning mechanism may be employed to engage and tension the folds within the tissue acquisition device. Said mechanical retraction or tensioning mechanism securely approximates the tissue folds such that a consistent and substantial fold of muscular tissue is presented for fixing the tissue folds together.

A fastening element or fastening assembly may also be employed to secure the tissue folds and create the division or divisions within the organ. Additionally, it may be preferable for the fastening assembly to clamp the tissue folds together prior to delivering the fastening elements to enhance the durability of the fastened section.

In similar fashion, a tissue acquisition device may be employed to secure tissue together, either in a dual fold (acquisition of a fold from both the anterior and posterior side of the organ), or single fold configuration (acquisition of one fold of tissue), at the GEJ to create an effective lengthening of the esophagus for treatment of GERD. A single or dual fold of tissue may be acquired at the cardiac notch (portion between the GEJ and the esophagus of the patient) and fastened to form a staple line parallel to the LC of the stomach.

Several aspects of the present invention were arrived at after experimentation with stomach and other body tissue and the challenges of acquiring and securing such tissue reliably. In particular, it is preferable for the device of the present invention to consistently approximate the tissue and tension it such that when the fixation elements or fasteners of the present invention are delivered, they consistently reach the outer fibrous layers of the organ wall, such as the muscularis and serosa of the stomach. Once these fibrous layers are secured appropriately according to the present invention, they will adhere, fuse or scar over to affect the desired fastening of the tissue folds. The devices of the present invention will likely need to maintain apposition of the two folds for 2–4 weeks, but that fusion of the tissue may take place as soon as 5–10 days following the procedure, or as long as 8–10 weeks. If tissue folds are secured inconsistently, or if insufficient compression is applied at the time of securement, complications such as rapid ischemic necrosis, gastric erosion, ulceration, and failure of the secured walls may result.

Various devices and methods for securing the tissue folds once they are approximated, may also include a stapling device, clamp or other fasteners. The fastening assembly may further be a flexible endoscopic stapler device, capable of being deployed within the lumen of the tissue acquisition device once the tissue folds are tensioned, said stapler then rotationally or longitudinally adjusted or automatically aligned within the tissue acquisition device to ensure correct alignment with the tissue folds, and clamped to deploy a staple line. This stapler is preferably deployed with force sufficient to displace much of the mucosal tissue out of the targeted fixation region prior to securing the two tissue folds together. A clamp device may be alternatively deployed instead of a staple to achieve both the clamping function and the fixation function. Said clamp device may include teeth or treads to allow tissue perfusion and cell growth for healing at the fixation region once the clamp is deployed. Fasteners such as rivets or clips may be deployed to secure the tissue.

Any of the fastening devices described herein may be bioabsorbable or biofragmentable, such that once the desired tissue healing has occurred, they dissolve or otherwise degrade leaving only the fixation region, now a tissue "bridge" (TB) sufficiently adhered or healed together to maintain the integrity of the pouch or partition, similar in some ways to the compression anastomosis tools referred to above. In addition, they may include coatings or other secondary features to aid healing, such as resorbable meshes, surgical felt, or tissue grafts.

The procedure of the present invention may be permanent in that the pouch or partitions would restrict the stomach indefinitely, or may be reversible (once weight loss is achieved, or reflux minimized) or revised (in the event pouch side needs to be modified). Further, if the physician so desires, techniques of the present invention may be augmented or assisted by the use of other techniques such as laparoscopy. Optionally, techniques of the present invention may be combined with other procedures such as the treatment of GERD or the transoral placement of a bypass prosthesis or other type of liner in the intestine to bypass of the hormonally active portion of the small intestine.

BRIEF DESCRIPTION OF THE DRAWINGS

FIGS. 4A–4H depict schematic drawings of the objects of the present invention for dividing and restricting, or partitioning a hollow body organ, namely the stomach as viewed from outside and inside the organ;

FIG. 7 depicts a cross section of the divided organ, showing the pouch excluded from the majority of the organ cavity by a healed in tissue bridge as constructed by the present invention;

FIGS. 15 and 15A depict a fastening assembly of the present invention, including a clamping device and a fastening device.

FIG. 17 depicts one embodiment of a fastening device of the present invention;

DETAILED DESCRIPTION OF THE INVENTION

The present invention provides, in part, for methods and devices for hollow organ division and restriction, more particularly providing methods and devices to perform a transoral, endoscopically mediated stomach reduction for purposes of, e.g., treating obesity.

Figure 1:
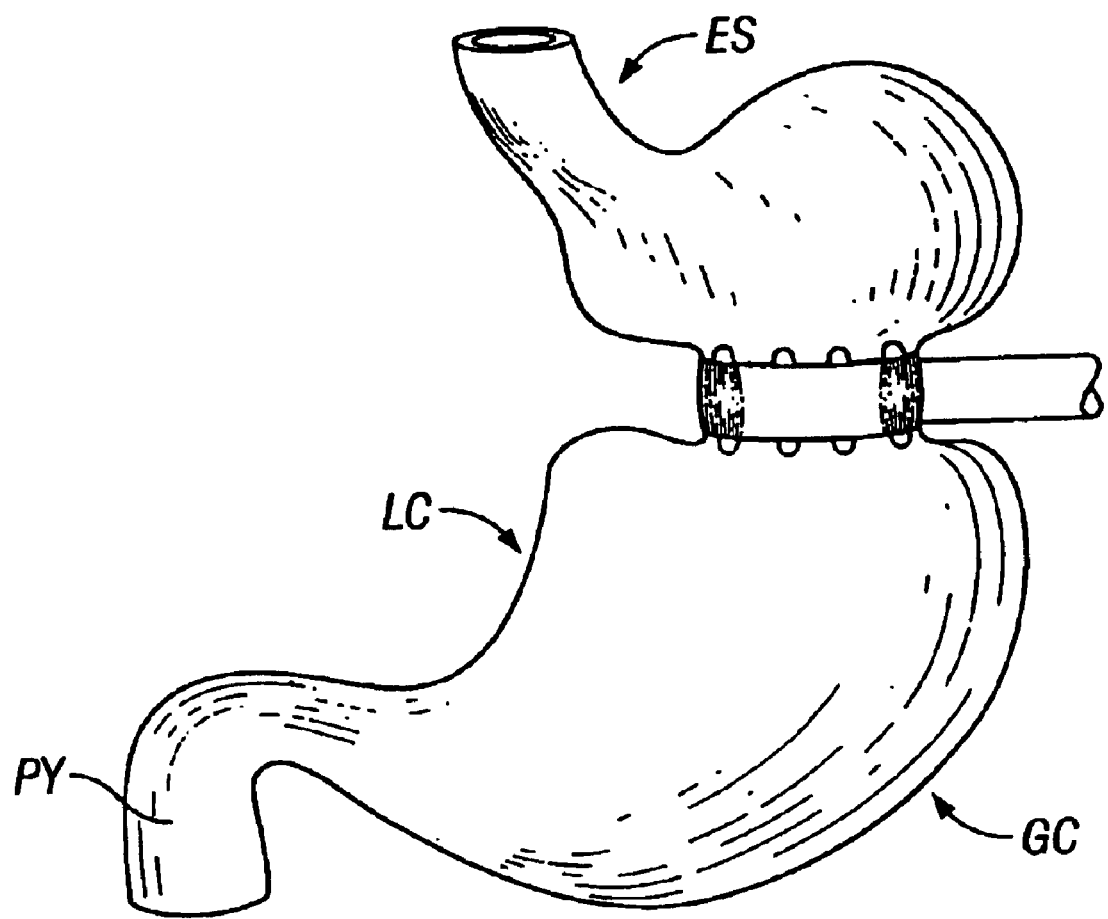
FIG. 1 depicts the prior art procedure commonly known as laparoscopic banding.
Figure 2:
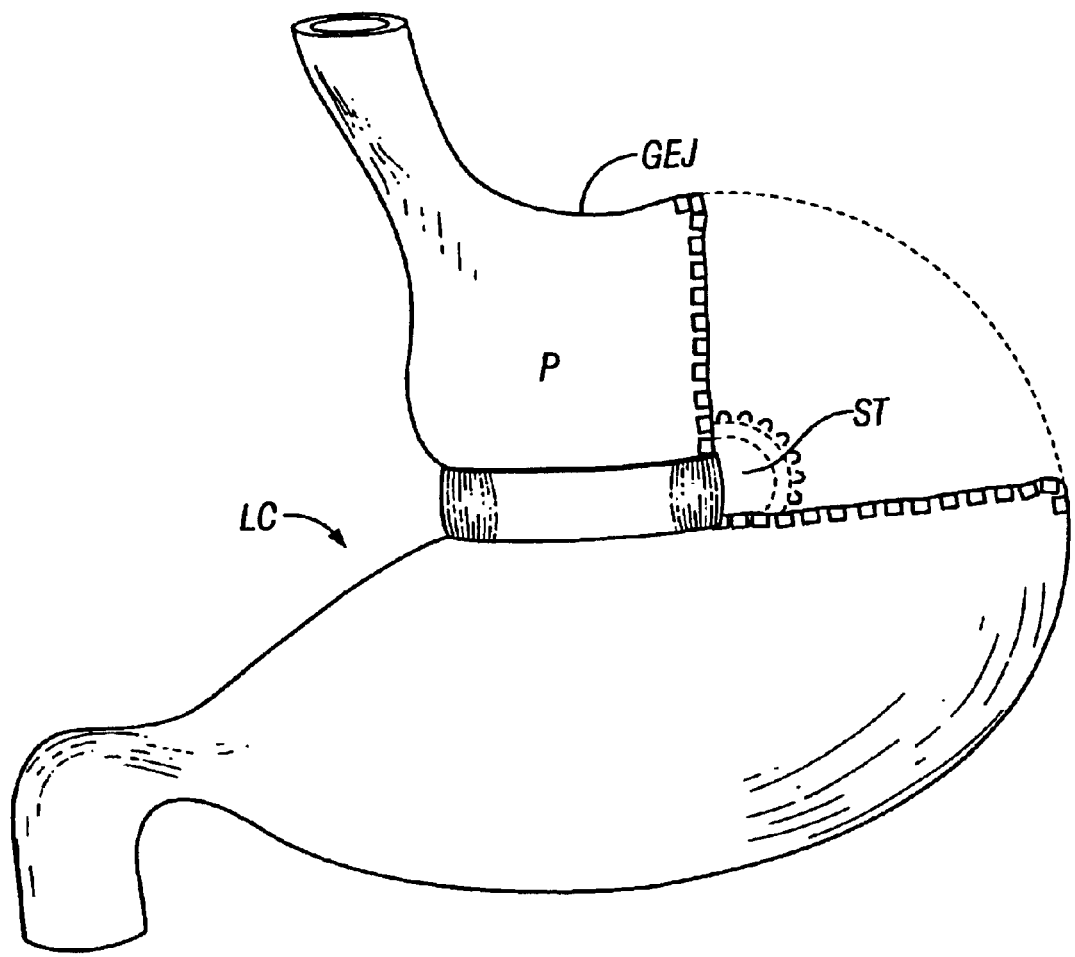
FIG. 2 depicts the prior art procedure commonly known as the vertical banded gastroplasty or "VBG"
Figure 3:
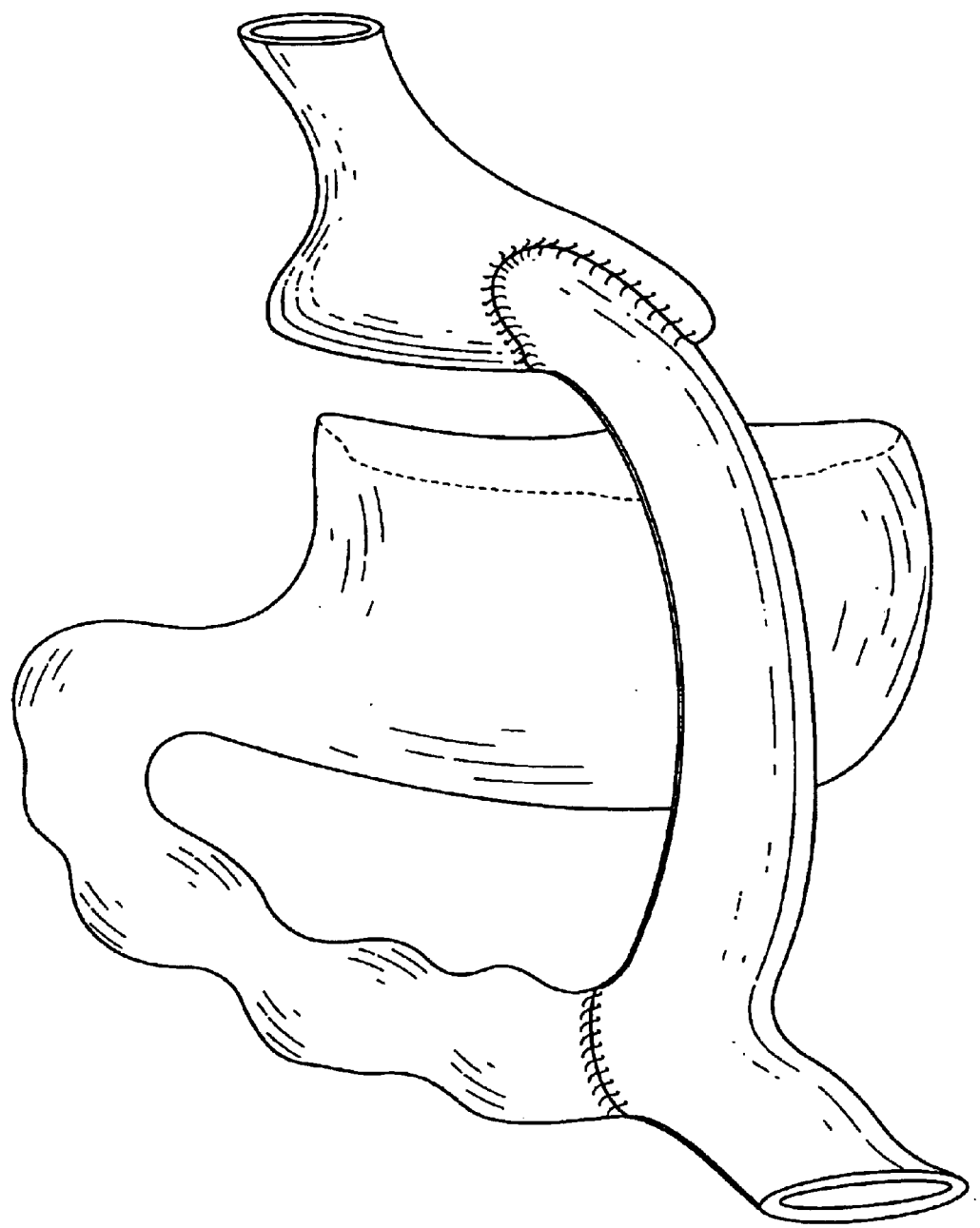
FIG. 3 depicts the prior art procedure commonly know as surgical Roux En Y procedure.
Figure 4A:
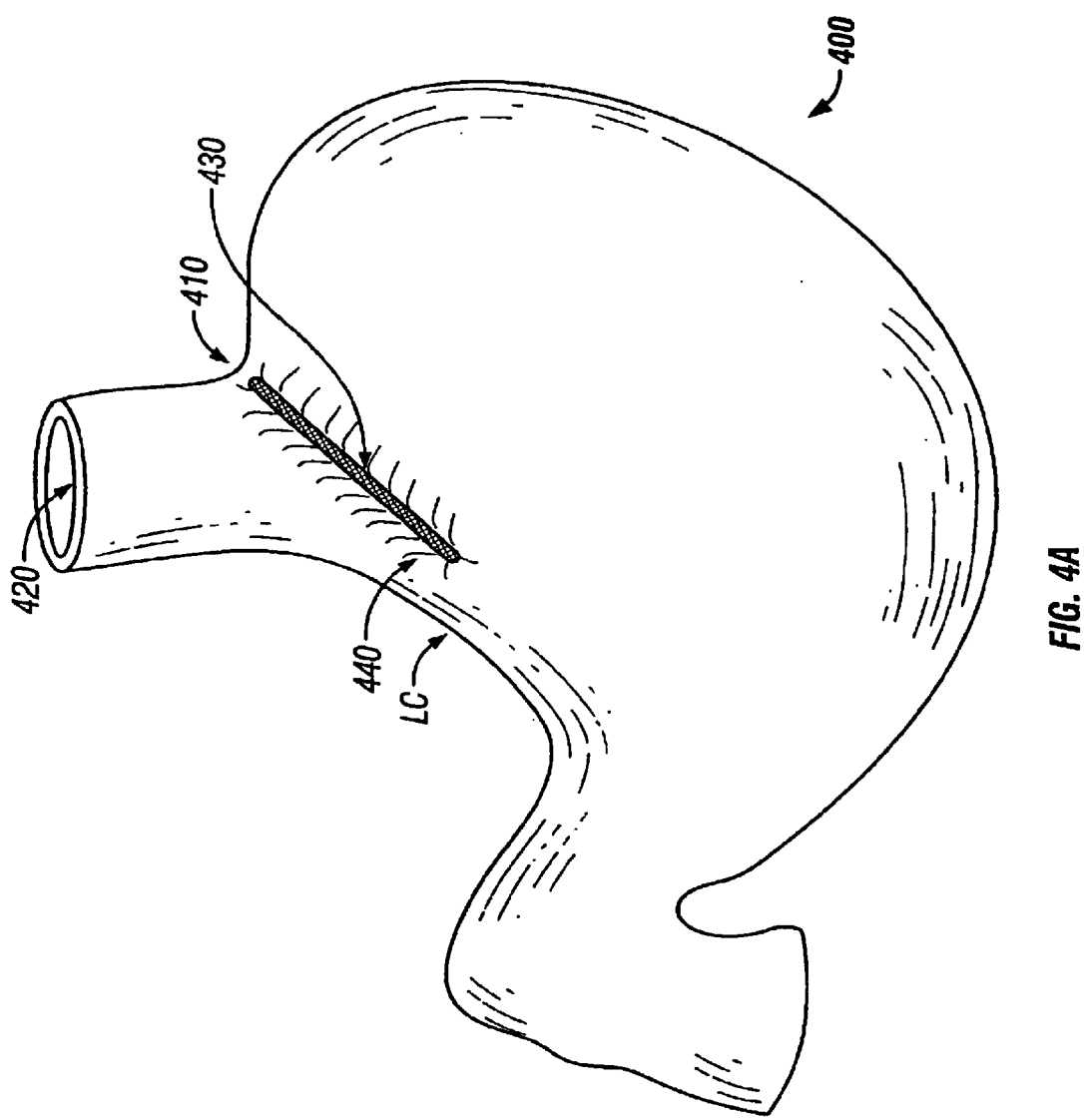
Figure 4B:
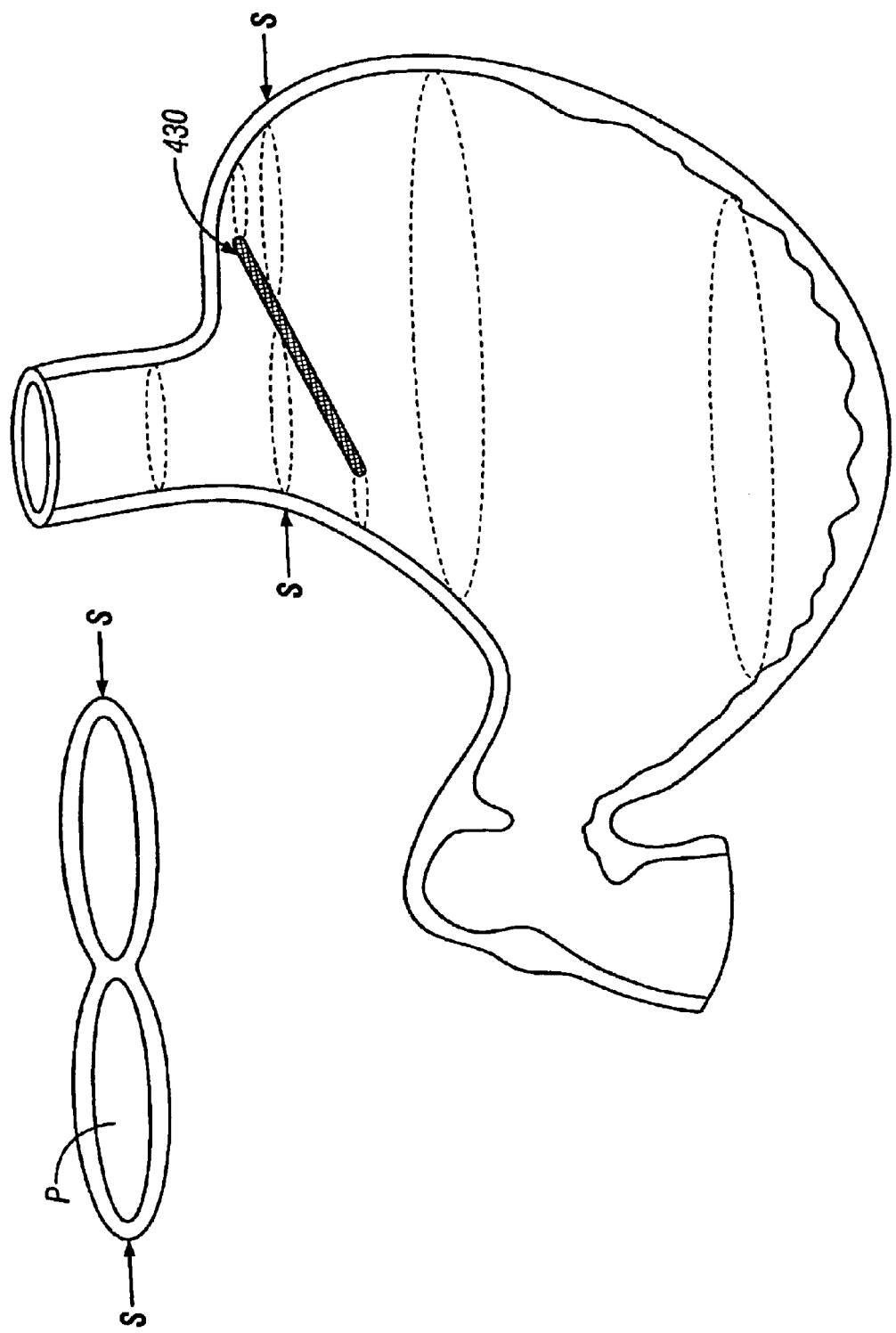

As previously discussed, the results of some clinical procedures of the prior art are shown in FIGS. 1–3, from a perspective external to the stomach. An example of a result of the procedure in one embodiment of the present invention is shown in FIG. 4A, depicting an external anterior view of a stomach organ 400, having an esophagus 410 (cut away to reveal the esophageal lumen 420), and further depicting a fastening line, or staple line 430, producing a pouch (P). Fastening line 430 is preferably positioned as close to the gastroesophageal junction (GEJ) at the base of the esophagus, and angled toward the lesser curve of the stomach (LC), leaving an approximate 1 cm gap between the LC and the end of fastening line. This gap, or stoma 440, operates to restrict food from emptying from the pouch, while still allowing communication between the pouch and the greater stomach volume for purposes of passage of digestive fluids and secretions. FIG. 4B depicts the organ division of FIG. 4A as a transparent section to further depict the cross section of the resulting division (pouch "P") created by fastening line 430 at section line S.

Figure 4C:
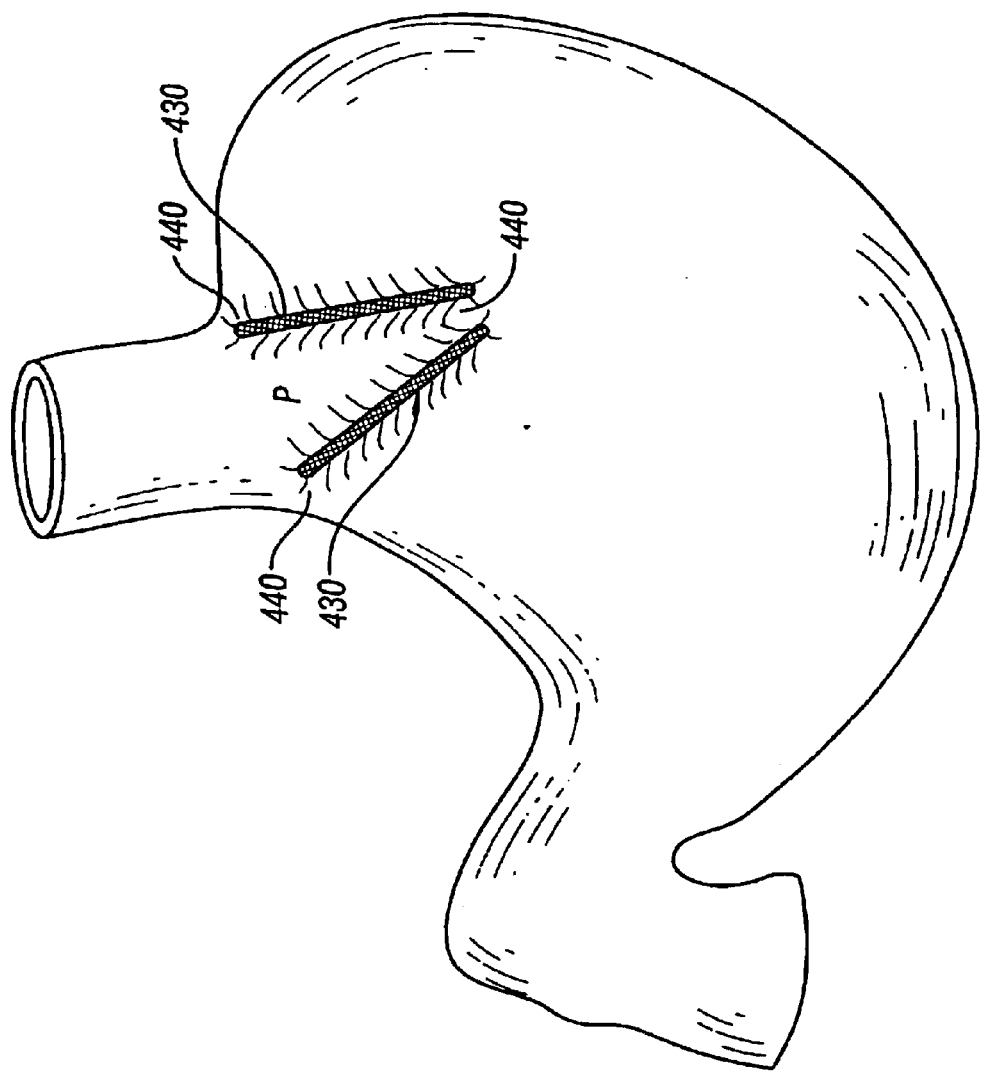
Figure 4D:
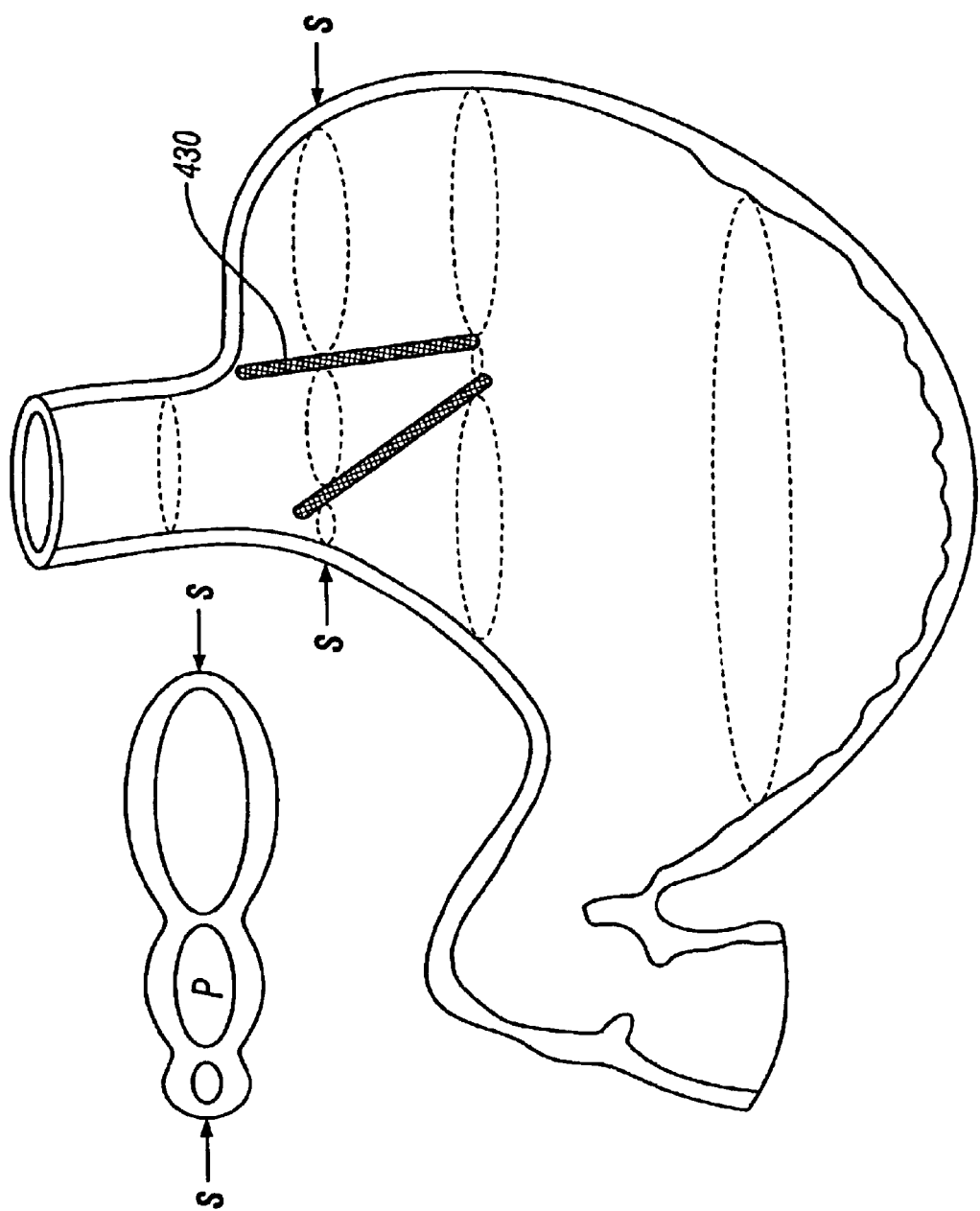

FIGS. 4C–4H represent alternative placements of the fastening line 430 to achieve various configurations of organ division, each having a potential clinical application depending on the preference of the physician and clinical needs of the patient. FIG. 4C depicts the same organ model as described in FIG. 4A, but with a plurality of fastening lines 430 placed in a funnel configuration to create partitions in the organ that form a pouch P between the fastening lines. In this embodiment, it may be desirable to leave several stomas or openings 440 to assist in organ function (e.g. digestion of food), while still restricting the volume of the pouch P. FIG. 4D depicts the organ division of FIG. 4C as a transparent section to further depict the cross section of the resulting division (pouch "P") created by fastening line 430 at section line S.

Figure 4E:
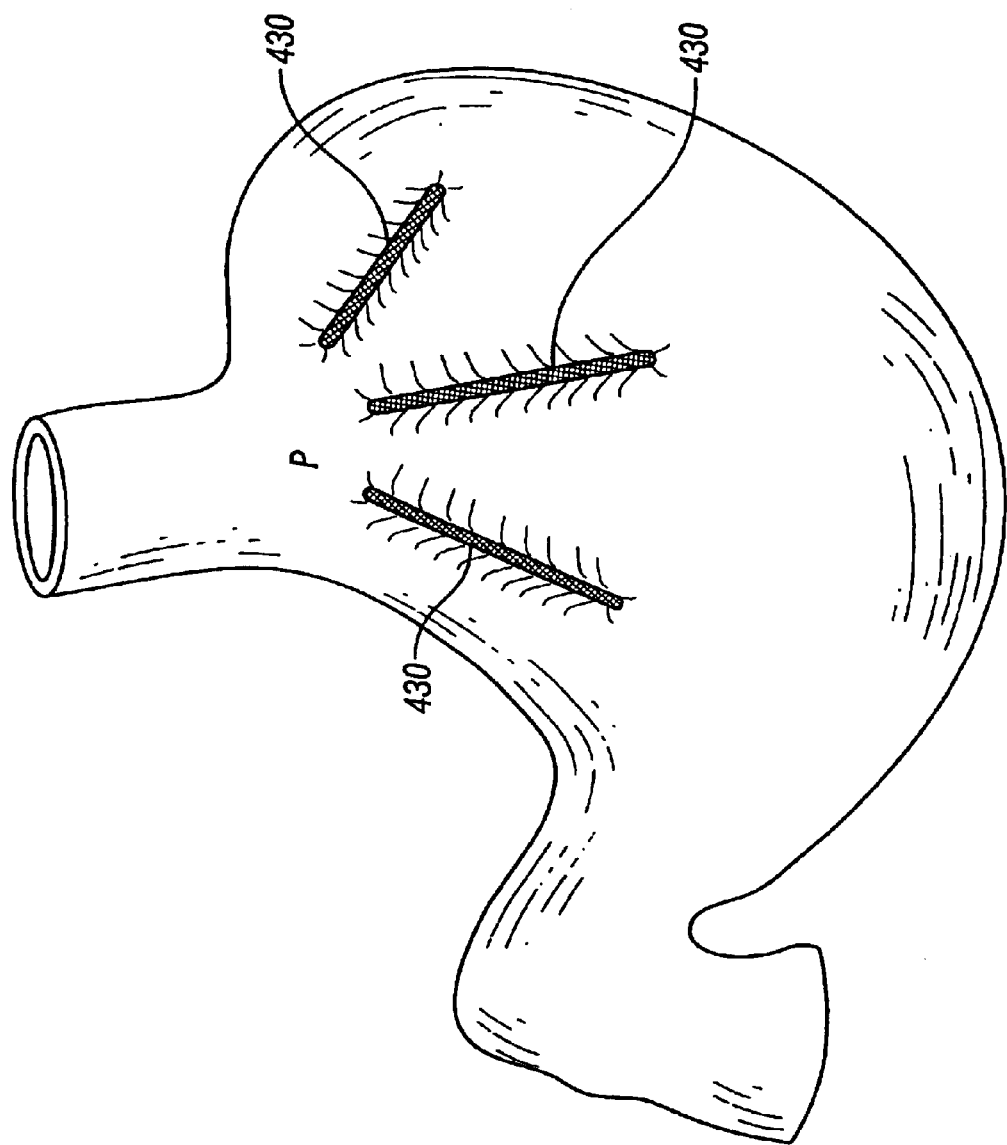
Figure 4F:
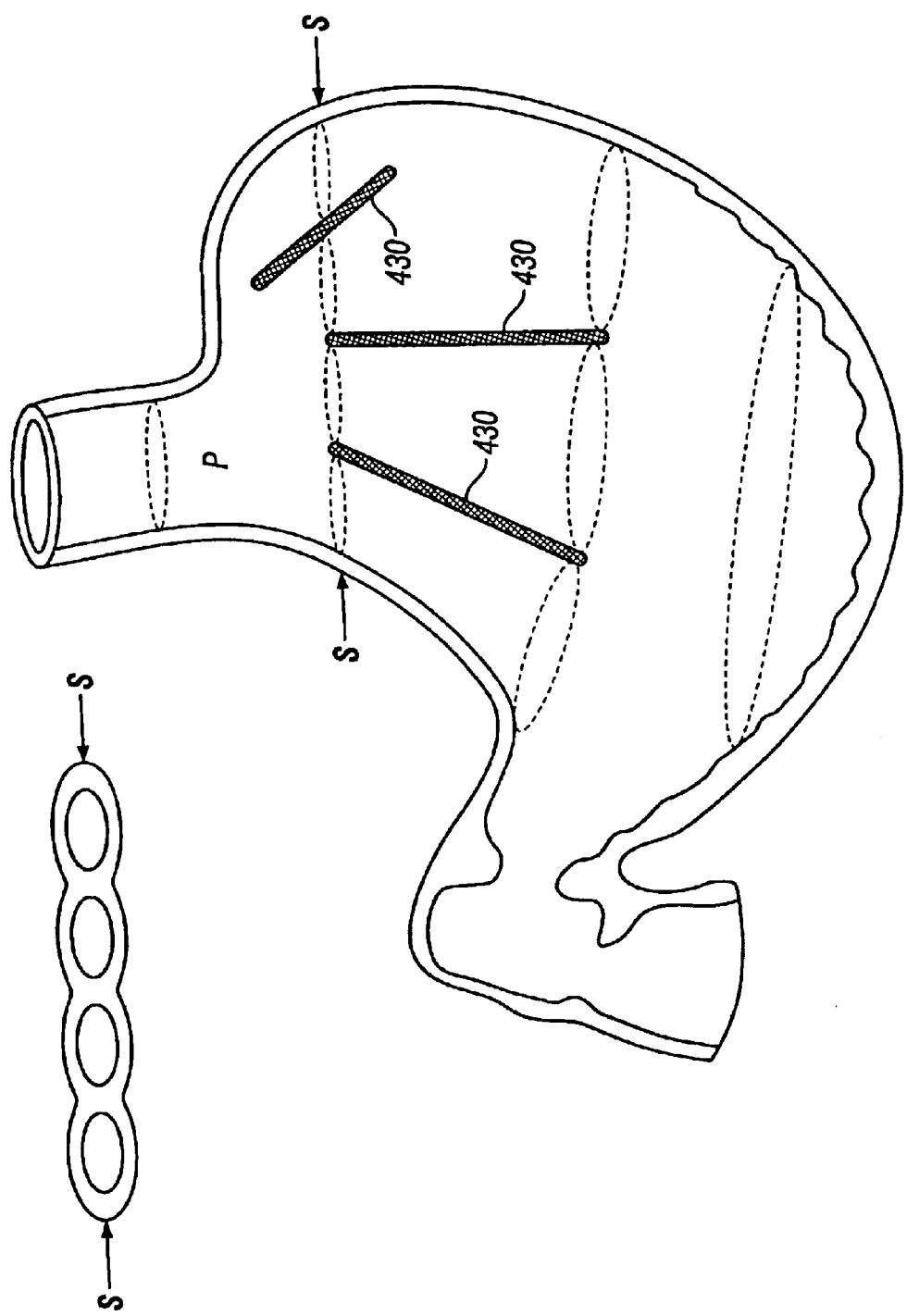
Figure 4H:
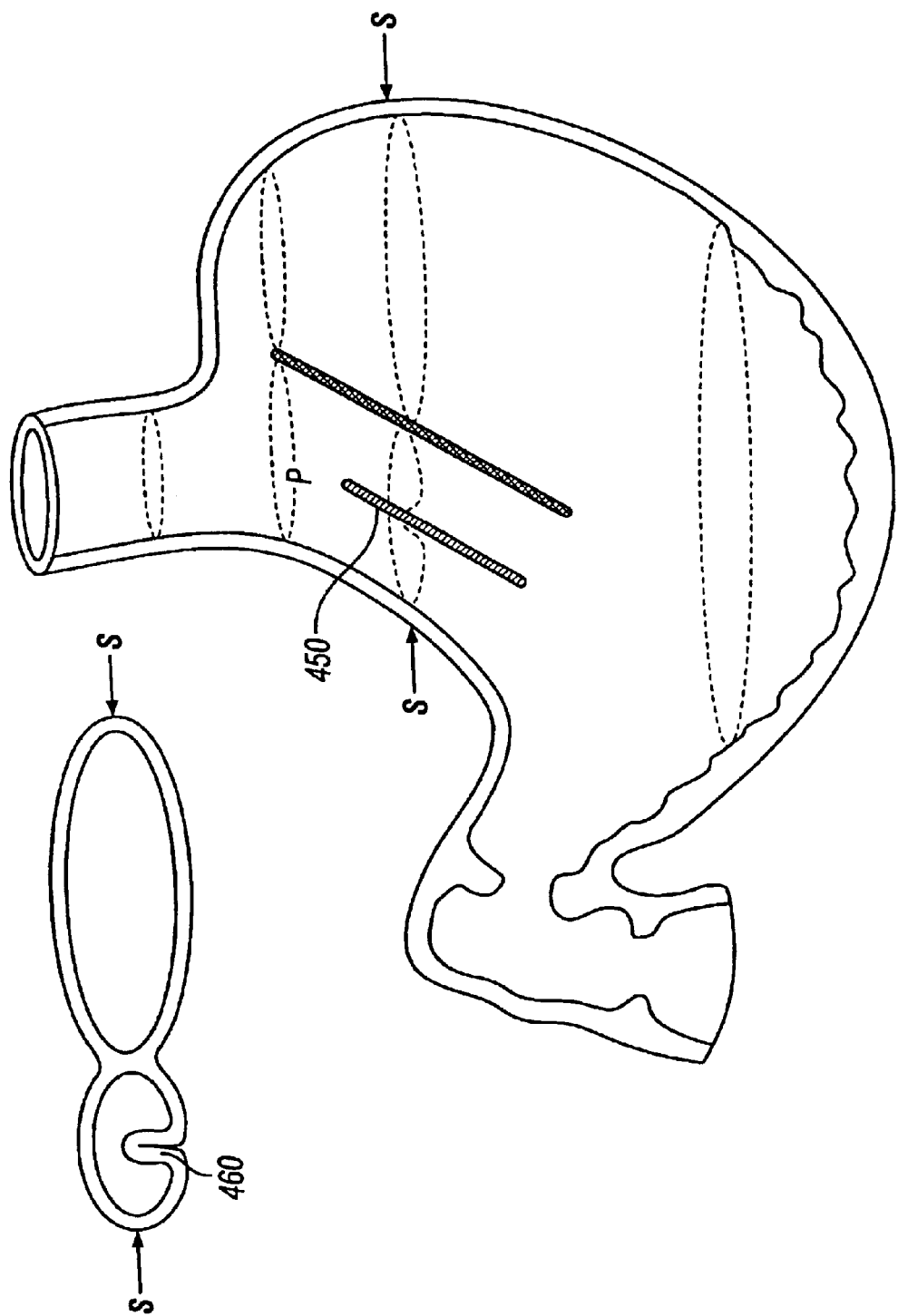

FIG. 4E depicts a further configuration of fastening lines 430, creating partitions within the organ for forming a restriction or pouch P. By using several fastening points or lines within the organ that fan out, intake can be restricted while still allowing the organ to function. Similarly FIG. 4F depicts the organ division of FIG. 4E as a transparent section to further depict the cross section of the resulting division (pouch "P") created by fastening line 430 at section line S. In yet another embodiment of the present invention, FIG. 4G depicts the placement of one fastening line 430 close to the GEJ and substantially parallel to the lesser curve of the stomach (LC) thereby forming a pouch or partition excluding the section of stomach below the esophagus from the majority of the stomach organ. An additional fastening line 450 may also be formed at or near the outlet of the pouch or partition, by either creating an additional dual fold fastening line to create a stoma, or by just acquiring one tissue fold, either the anterior or posterior wall of the stomach to create a pleat 460, thereby also narrowing the outlet or creating a stoma. Such a division and single fold tissue pleat 460 are depicted in FIG. 4H showing a transparent sectioning of a divided stomach.

It is anticipated that the placement of fastening lines 430, may vary from those depicted herein, as is necessary for a physician to achieve a desired clinical effect, or to overcome variations in the anatomy of the patient. Such configurations that utilize the methods and devices of the present invention are contemplated to be within the scope of this disclosure. In addition, a fastening line 430 as referred to herein, may be a line of fastening elements placed simultaneously or serially until the desired result is achieved. They may also be in the form of a clamp or other fastening element, as described herein, or as known in the art for securing tissue together.

Figure 5:
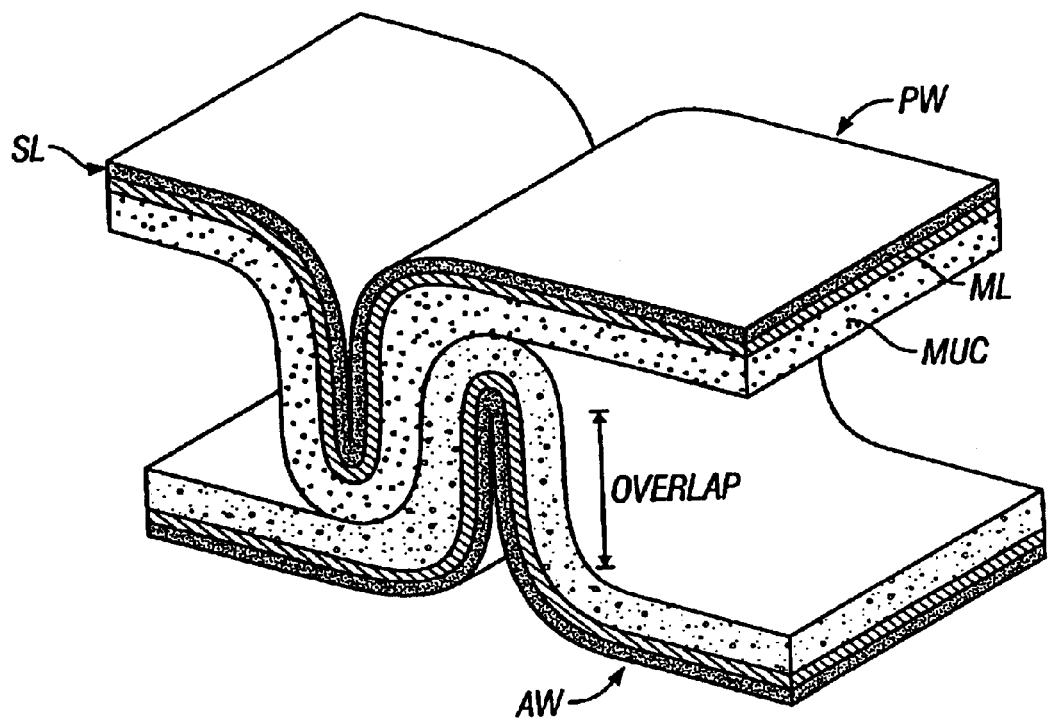
FIG. 5 shows a schematic depiction of a cross section of two tissue folds (anterior and posterior stomach wall) as they would be acquired and tensioned by the tissue acquisition device of the present invention (devices deleted for clarity)
Figure 6:
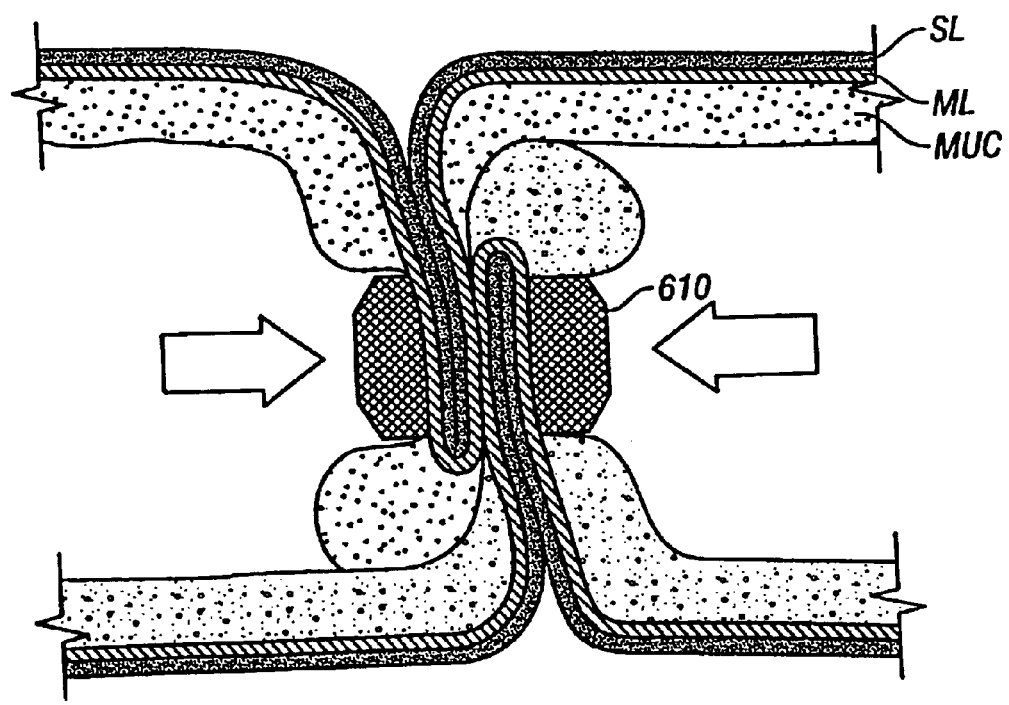
FIG. 6 depicts a cross sectional view of the clamping of the two tissue folds to ensure approximation of the fibrous tissue layers, and the positioning of a clamp or fastener of the present invention.

FIGS. 5, 6 and 7 depict cross sectional schematic views of the procedure of the present invention from the perspective of the tissue being manipulated. In FIG. 5, the posterior wall of the stomach (PW) and the anterior wall of the stomach (AW) are shown in the configuration they will take once the tissue acquisition device of the present invention has been activated (device not shown for clarity). Tissue layers represented are the serosal layer (SL), the muscularis or fibrous muscular layer (ML), and the mucosal layer (MUC). One feature of the present invention is to acquire the tissue such that it is positioned with a certain amount of fibrous tissue overlap (Overlap) prior to fastening in a configuration akin to a lap joint. The amount of the overlap can vary and needs only to be sufficient enough to result in healing of the fastened sections, thereby creating a tissue bridge (TB) along the length of the fastened tissue. Said tissue bridge may be formed of various layers of the stomach and may include scar tissue and other elements of effective wound healing.

In addition, it may be advantageous to further approximate the Overlap section by clamping the tissue to be fastened as depicted in FIG. 6. When clamps 610 applies a clamping force to the overlapped section, the less fibrous lining of the stomach, the mucosa (MUC), is compressed and squeezed thin to minimize its presence within the fixation zone. In doing so, the fibrous muscularis and serosal layers that are more responsive to healing can be more closely approximated. Finally, FIG. 7 illustrates the formation of a tissue bridge (TB) between the two tissue folds, demonstrating that each pouch or lumen is re-paved with mucosal tissue and fasteners are covered by mucosa such that only the mucosa is exposed to the acids of the stomach, but the tissue bridge itself is formed of the various fibrous tissue layers, including scar tissue.

Devices

Figure 12:
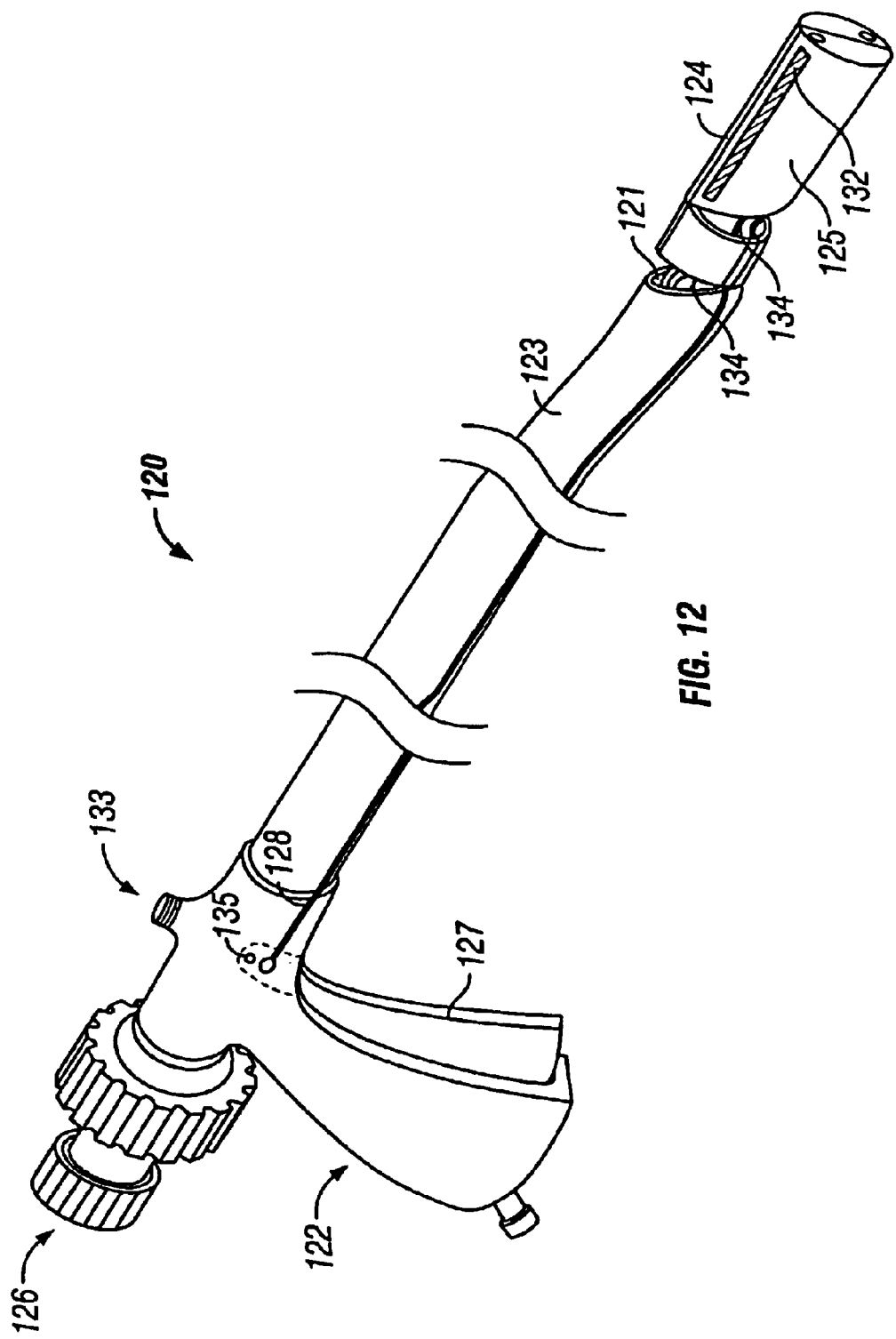
FIGS. 12, 12A, 12B and 12C depict one embodiment of a tissue acquisition device of the present invention, including detail on an articulating feature used as a tensioning device to further approximate the acquired tissue folds.

FIG. 12 shows the tissue acquisition device 120 of the present invention having a proximal and distal end and a main lumen 121 therebetween. Device 120 has a handle portion 122, and a main body portion 123 having one or more lumens (not shown) and terminating in a distal end, said distal end preferably segmenting into first and second jaw members 124 and 125 respectively, each jaw member having a tissue acquisition port 132 housed therein. Each port 132 is in fluid communication with one of the lumens of the main body portion 123 and connected to filler port 133 located on handle portion 122.

Main body portion 123 may be bendable, having a shaft made of resilient plastic such as polyurethane, silicone, PVC or a laminate all optionally reinforced with a wire, or made of a composite construction of more than one material, or articulable, such as formed of a slotted tube connected to a pull wire in the proximal handle (not shown), to allow the operator to achieve flexion of the main body portion or distal tip by operating the pull wire. Such flexibility allows for smooth introduction down the esophagus and into the stomach, as well as optimal positioning within the stomach prior to tissue acquisition. In addition, handle portion 122, preferably includes a main port 126, through which various devices such as an endoscope or fastening assembly of the present invention may be passed to monitor and complete the procedure of the present invention.

Figure 12A:
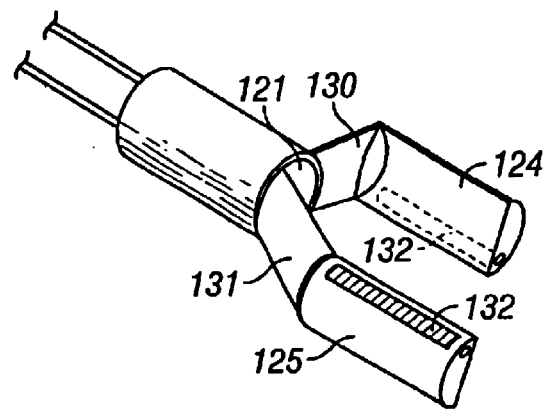
Figure 12B:
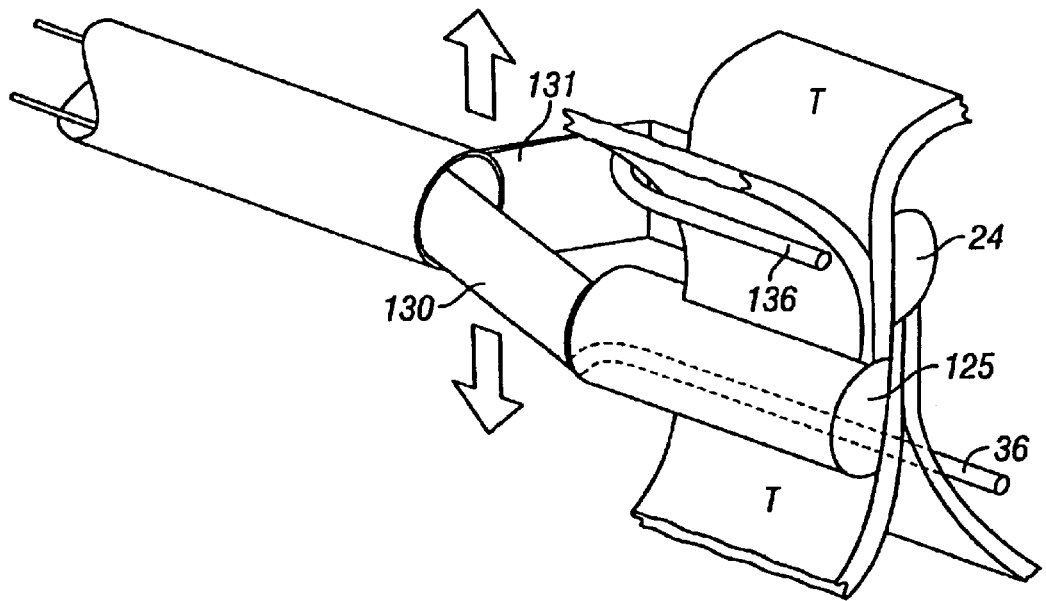
Figure 12C:
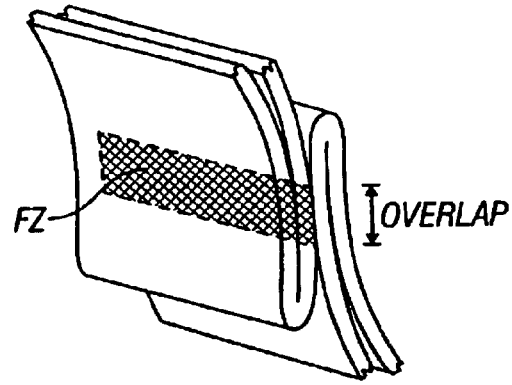

It may be necessary or desirable to employ a further tensioning mechanism at device 120 distal end to assist the use of vacuum to acquire the desired tissue. The embodiment depicted in FIGS. 12A and 12B, shows first and second hinging members 130 and 131, respectively, formed as part of main body 123 and connected to each of distal end jaws 124 and 125. Hinging members 130, 131 can be formed in multiple ways, but are shown in FIG. 12 as being formed by two crescent shaped cutaways 134 spaced longitudinally along the shaft of main body 123 and at 180 degree rotations from one another. In operation, a lever 127 is pivotally connected to the main handle body 122 by pin 135. Pull cables 128 (only one shown) are fixedly connected to lever 127 and jaws 124 and 125 such that when lever 127 is deployed jaws 124 and 125 separate in a scissoring motion as depicted in FIG. 12B. Actuation of hinging members 130 and 131 act to further tension the tissue already acquired in vacuum ports 132 and ensuring the fixation zone (FZ) includes the appropriate amount of serosal overlap as depicted in FIG. 12C. Optional guide rods 136, may be affixed to jaws 124 or 125 or both, to assist in tissue tensioning and manipulation (tissue shown here as T).

Figure 13:
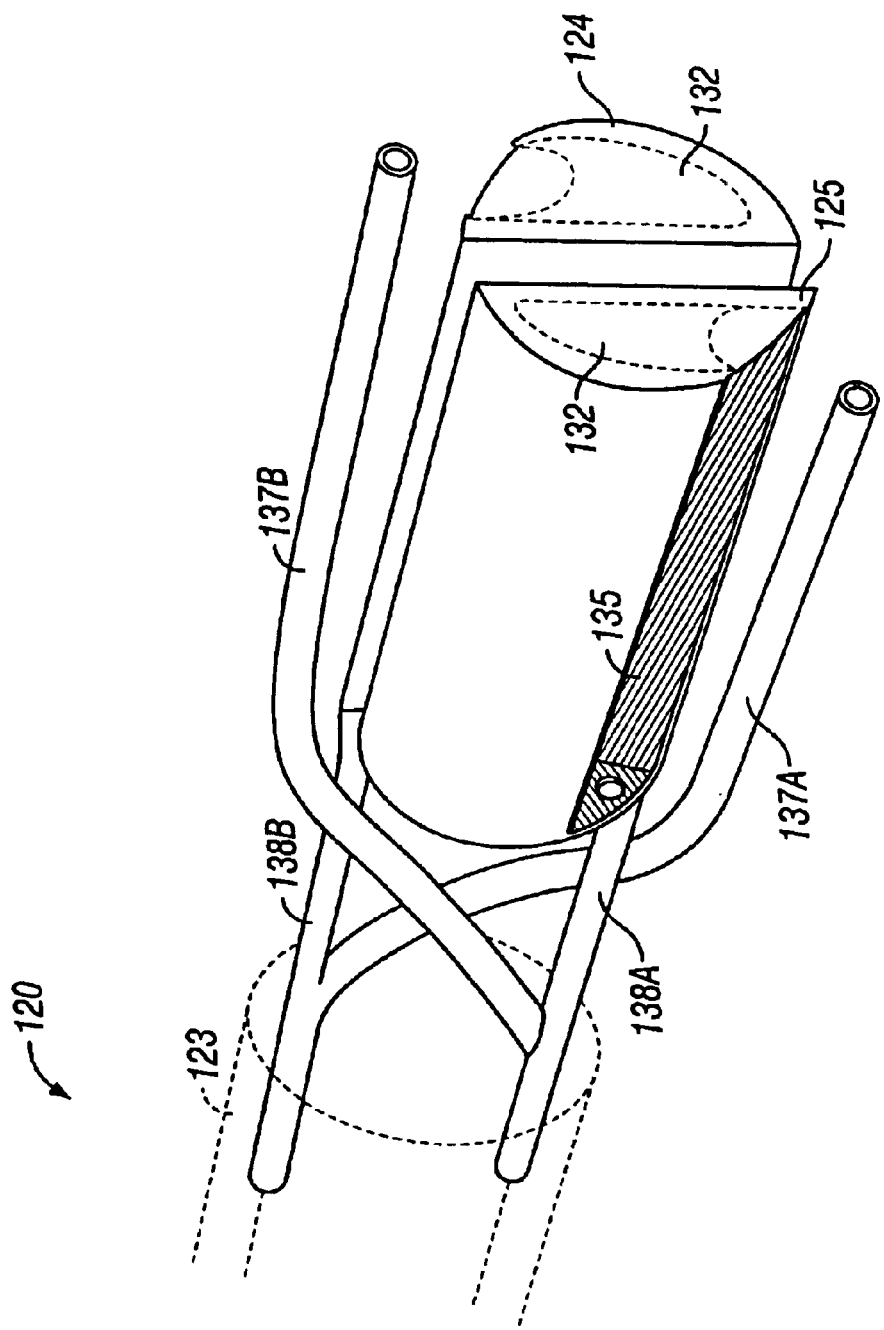
FIG. 13 depicts another embodiment of a tissue acquisition and tensioning device of the present invention.

FIG. 13 depicts a more detailed showing of the jaws 124 and 125 of tissue acquisition device 120, including an alternative embodiment of a guide rod mechanism. Each jaw (124, 125) is equipped with a vacuum port 132, each located at 180 degrees from the other to allow tissue to be acquired from opposite sides of the organ while allowing the maximum axial depth within the jaw body. Port opening 132 may extend approximately 1 inch longitudinally along the jaw body, and approximately 0–5 cm into the jaw body, depending on the amount of tissue to be acquired (dotted lines depict various depths of the port). It is also within the scope of the present invention for such vacuum ports 132 to be configured in the form of suction cups, or formed of fenestrations within the jaw. Vacuum ports 132, are in fluid communication with tubes 138A and 138B, which run the length of the tissue acquisition device main body, and terminate at filler port 133 as earlier described to allow vacuum to be activated at the ports. In this alternative embodiment, each jaw (124, 125) is equipped with a guide rod 137A, 137B consisting of a rigid bar members affixed to respective tubes 138A and 138B proximal of the communication between the tubes 138A and 138B and each respective jaw body, and further curved to extend longitudinally along the jaw body 180 degrees from port opening 135 on respective jaws. Guide rods act as a stay to further assist in tissue manipulation and tensioning. This embodiment functions similarly to that already described in FIGS. 12, 12A and 12B.

Figure 14:
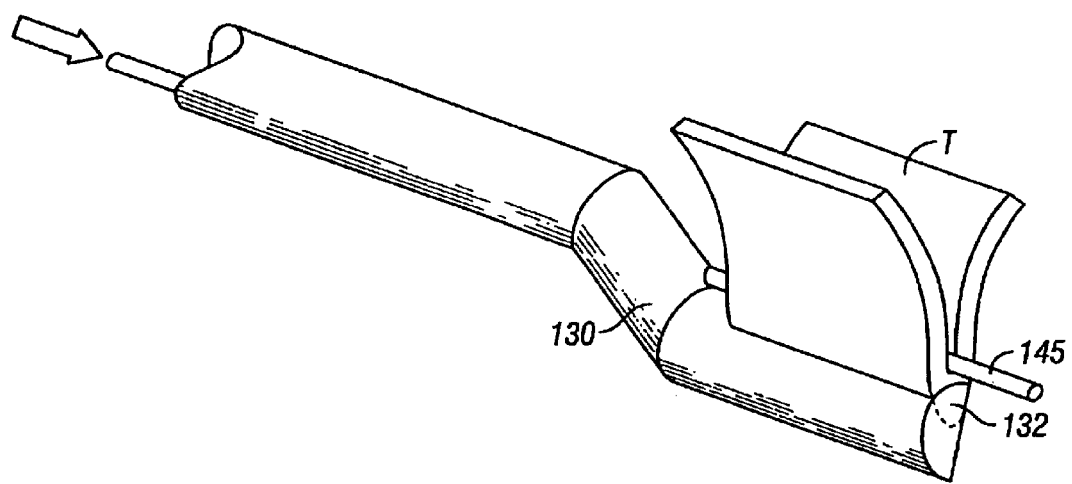
FIG. 14 depicts another embodiment of a tissue acquisition and tensioning device of the present invention (only one arm of the device is shown for clarity)

FIG. 14 shows yet another embodiment of the distal end of the tissue acquisition device of the present invention, incorporating both the hinging members 130, 131 (not shown) of FIG. 12, and an additional mechanical post 145 inserted down the lumen of tissue acquisition device 120 once tissue has been acquired in vacuum port 132, but prior to activating the hinging members 130, 131, to act like a skewer and further secure the acquired tissue in place.

In some cases, the jaws 124, 125 and preferred tensioning mechanism of tissue acquisition device 120 are adapted such that the insertion of fastening assembly 150 through the distal end of tissue acquisition device 120, activates (by spreading or displacing) the tensioning mechanism. This passive activation of the tensioning mechanism obviates the need for additional pull wires, cables or levers to control the tensioning process. It is also within the scope of the present invention that the tensioning mechanism involves twisting of the tissue folds once they are approximated by the tissue acquisition device.

Figure 15:
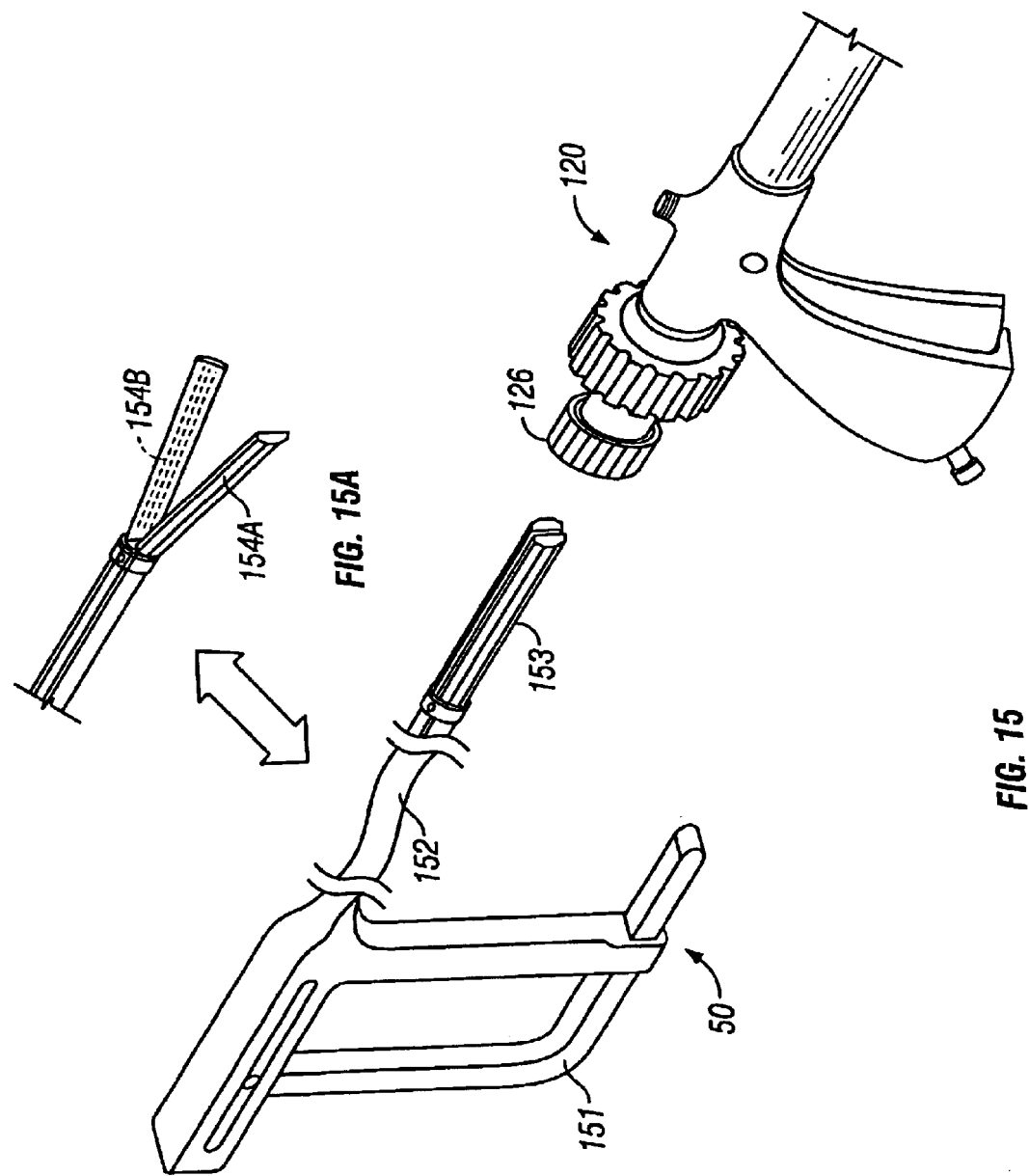
Figure 16:
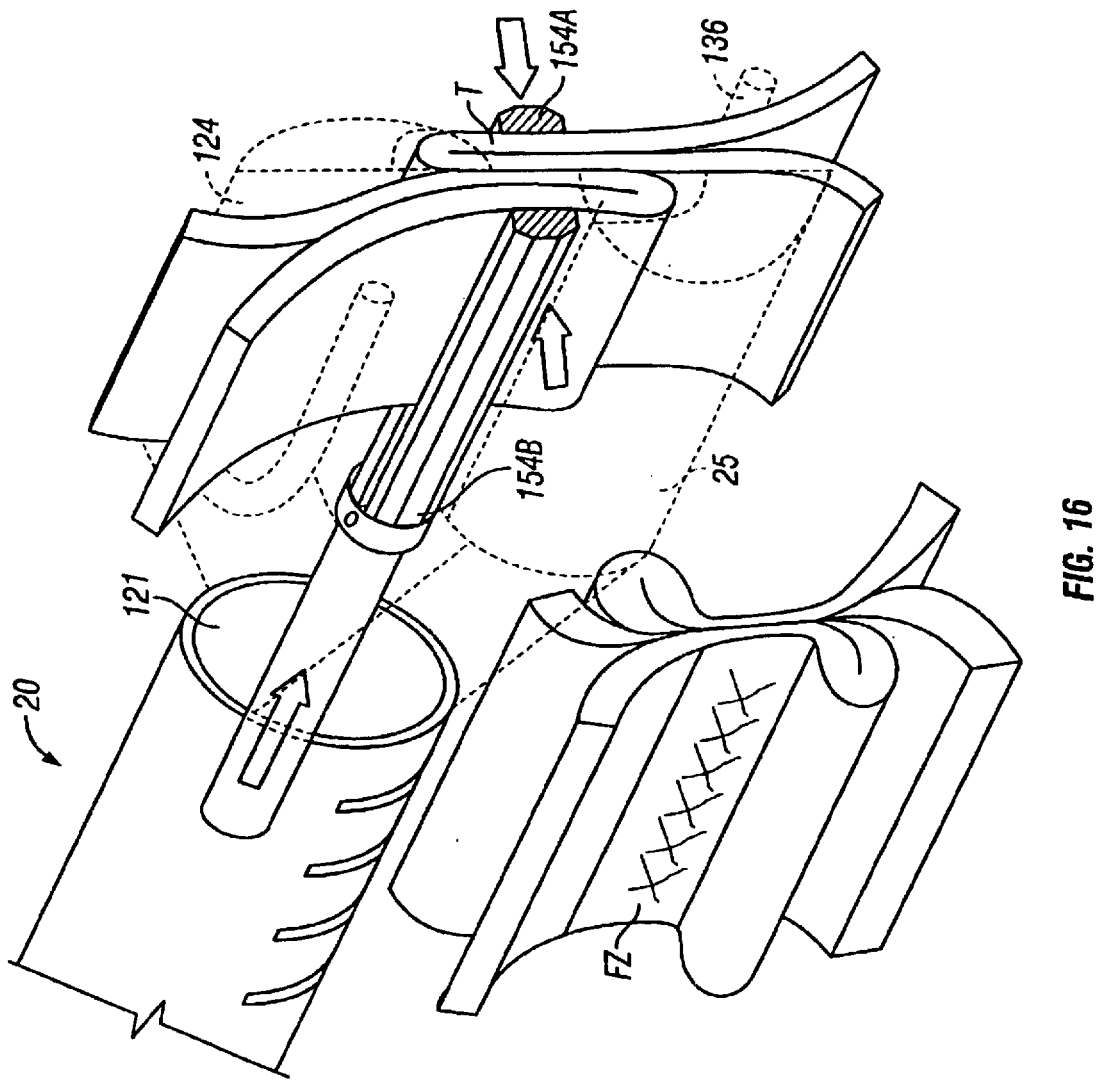
FIG. 16 depicts the operation of the fastening assembly of FIG. 15 through the tissue acquisition device (distal end omitted for clarity) to clamp and fasten tissue folds as taught by the present invention.

FIG. 15 shows fastening assembly 150, consisting of a fastening assembly handle 151, fastening assembly main body 152, and fastening assembly clamping portion 153, having clamping jaws 154A and 154B. FIG. 15A depicts fastening assembly clamping portion 153 in an open configuration (its default setting). In use, handle 151 is slightly engaged to bring jaws 154A and 154B of clamping portion 153 together such that fastening assembly 150 can be inserted into the main port 126 of tissue acquisition device 120. Once inserted, FIG. 16 depicts placement of jaws of fastening assembly inserted within distal end of tissue acquisition device 120 (distal end shown in dotted line configuration). Following insertion of the fastening assembly down the main lumen 121 of the tissue acquisition device 120, fastening assembly handle 151 is actuated to fully engage jaws 154A and 154B into acquired tissue T. Once tissue is clamped, fastening elements can be deployed into the clamped tissue (fixation zone (FZ)) as further described below.

FIGS. 17–18 show various embodiments of fastening elements deployed by the fastening assembly of the present invention. FIG. 17 depicts an implantable clamp member 170, including a penetrating clamp portion 171 having post portions 175, and a receiving clamp portion 172, having receiving members or holes 176 adapted for interface with posts 175. One or other of said clamp members may include a patterned or protruding surface on tissue engaging surface 174 to lessen the potential for tissue necrosis and aid in healing. In addition, tissue engaging surface 174 may include spikes or other penetrating elements (not shown) to minimize slippage while clamping. In further embodiments, implantable clamp member 170 may be formed in a curved configuration to assist in creating optimal pouch geometry. Further, implantable clamp member may be formed of various materials that are either permanent or biofragmentable such as Delrin®, polyglycolic acid, lactomer, polyester, polydiaxinon, steel, titanium or NiTi.

In operation, penetrating clamp portion 171 and a receiving clamp portion 172 would be loaded into the respective jaws of fastening assembly 150 prior to insertion of the fastening assembly into the tissue acquisition device, and deployed into the acquired tissue upon clamping of the fastening assembly onto the deployed tissue. It should be further noted that penetrating clamp portion 171 and a receiving clamp portion 172 may be deployed as two separate pieces, or may be hingedly connected in a similar fashion to the clamp jaws 154A and 154B of the fastening assembly 150.

Figure 18A:
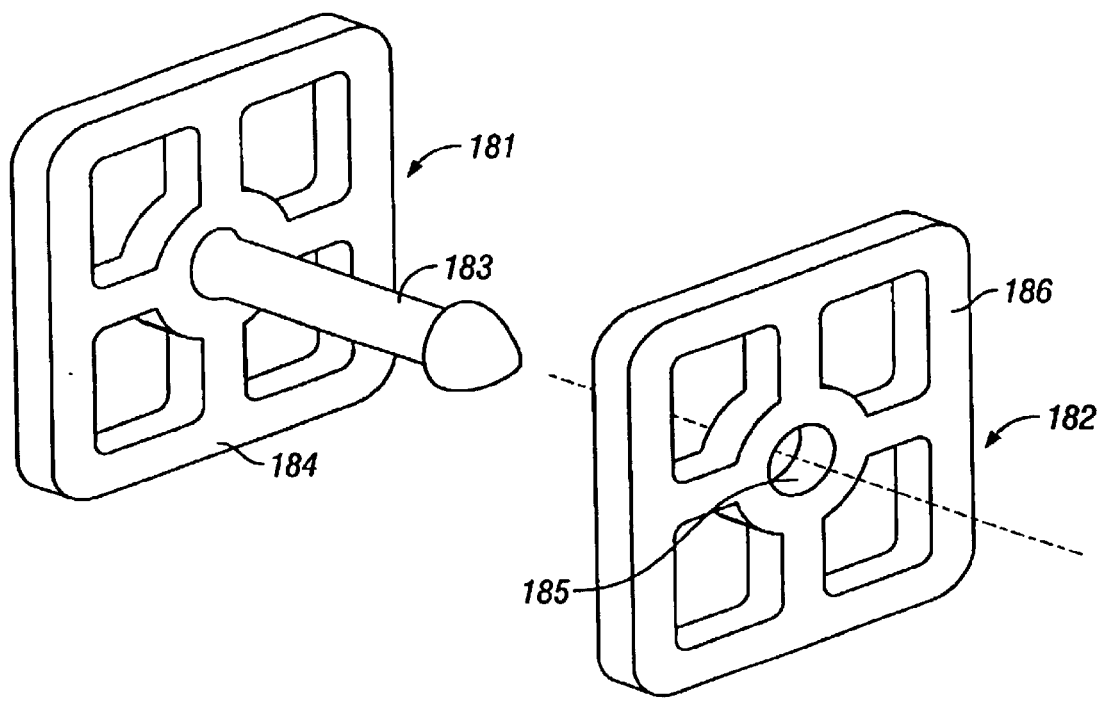
FIGS. 18A and 18B depict another embodiment of a fastening device of the present invention in an undeployed and deploying configuration.
Figure 18B:
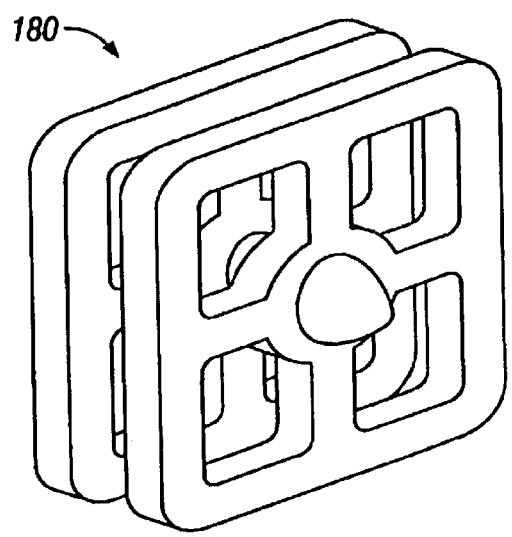
Figure 19:
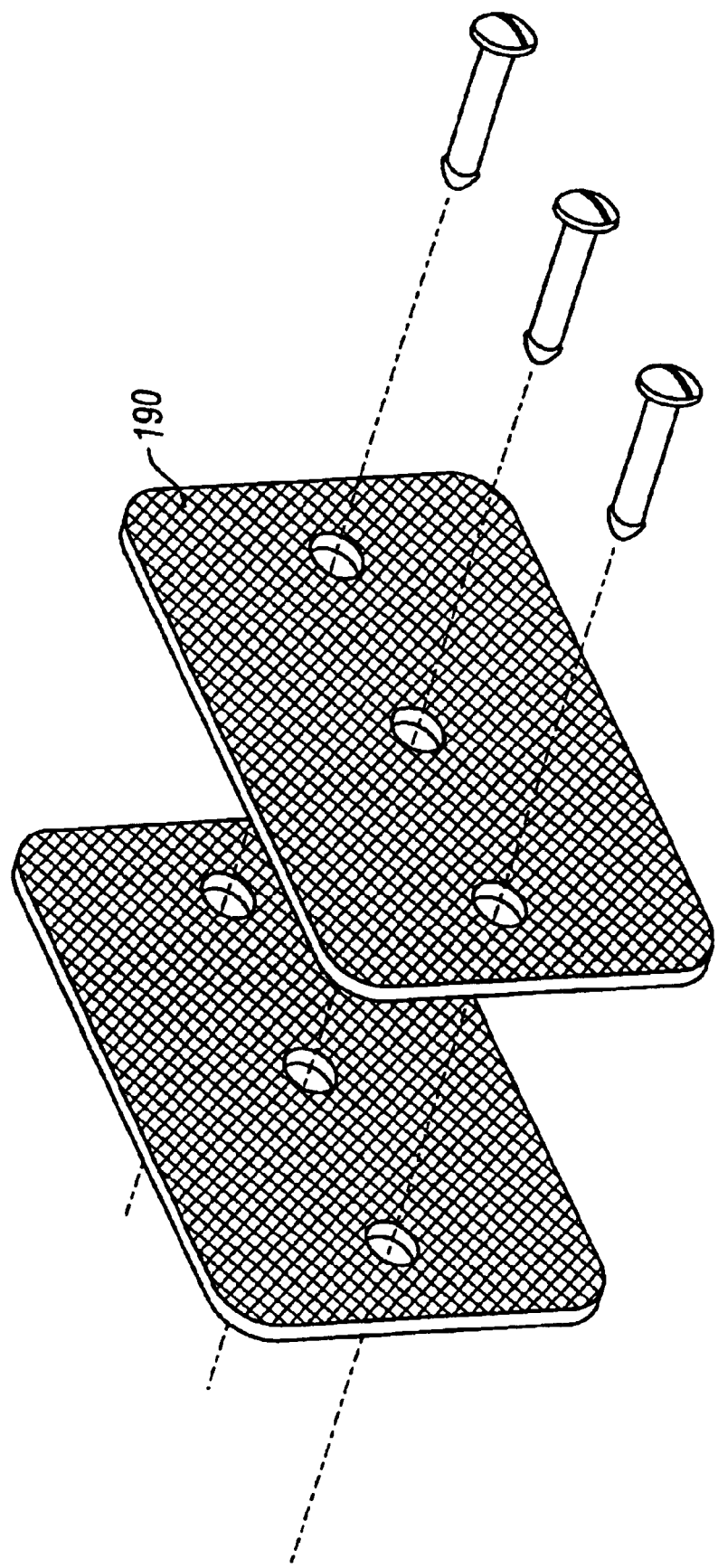
FIG. 19 depicts yet another embodiment of a fastening device of the present invention.

FIG. 18A depicts fastening elements 180 consisting of discrete rivets having a penetrating rivet portion 181, having a post portion 183 and a body portion 184, and a receiving rivet portion 182, having a receiving element 185 and a body element 186. Such rivets can be formed of materials that are either permanent or biofragmentable such as Delrin®, polyglycolic acid, lactomer, polyester, polydiaxinon, steel, titanium or NiTi, and can be deployed in parallel with other rivets or sequentially, depending on the desired outcome. FIG. 18B depicts the fastening element of the present invention in it's deployed state. As shown in FIG. 19, fastening elements or rivets may be coupled with a material 190 to assist in tissue ingrowth and healing. Such materials may be meshes, grafts, microporous membranes or biomaterials such as collagen or porcine biointestinal submucosa (Biosis®, Cook, Inc.) In operation, such materials may either be adhered to the fastening element, or provided as a separate element to be placed within the fastening assembly jaws prior to clamping and deploying fastening elements.

Figure 20A:
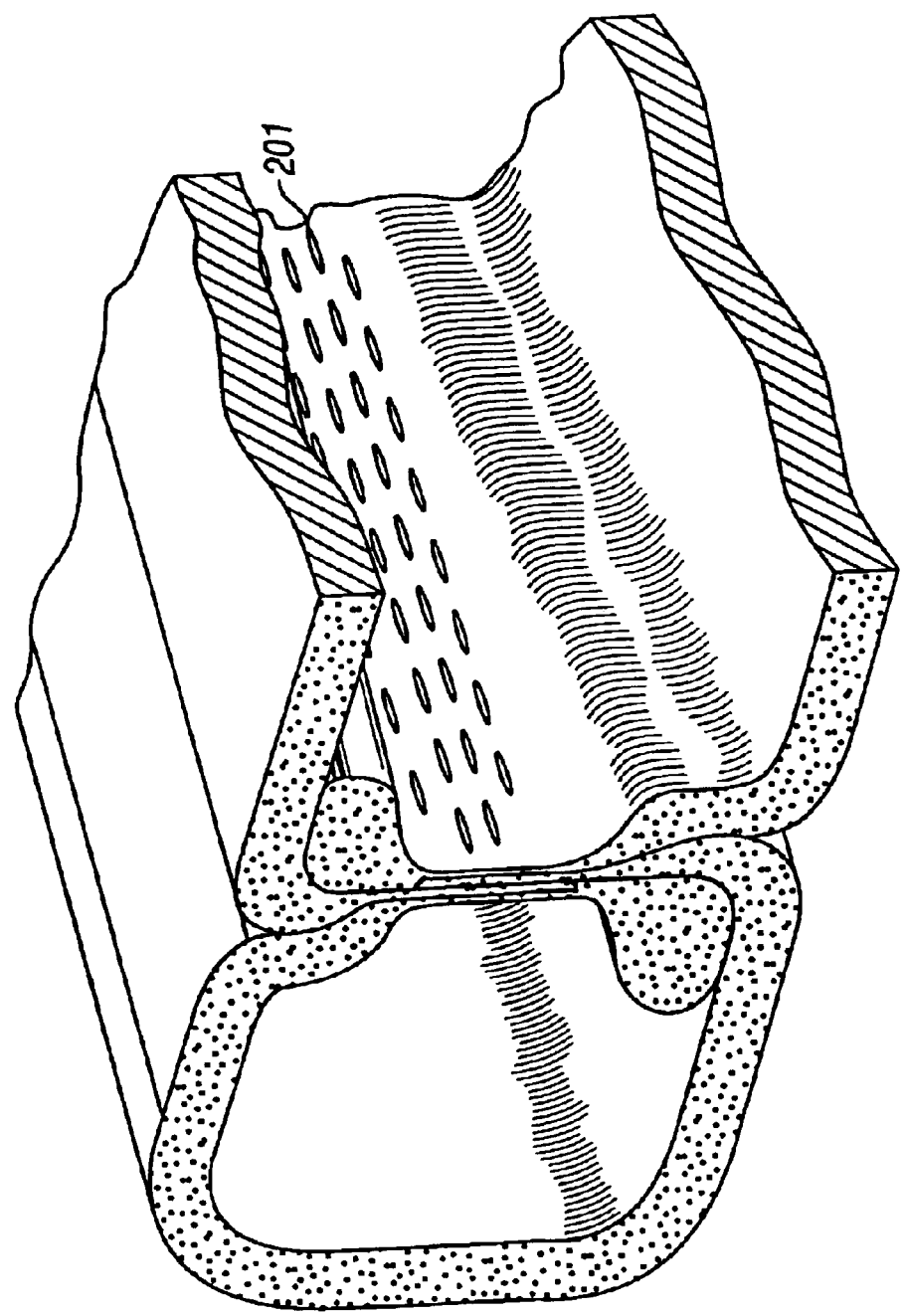
FIGS. 20A and 20B depict a cross sectional, perspective view of representative fastening devices of the present invention deployed to approximate two tissue folds of a target organ to be divided or restricted.
Figure 20B:
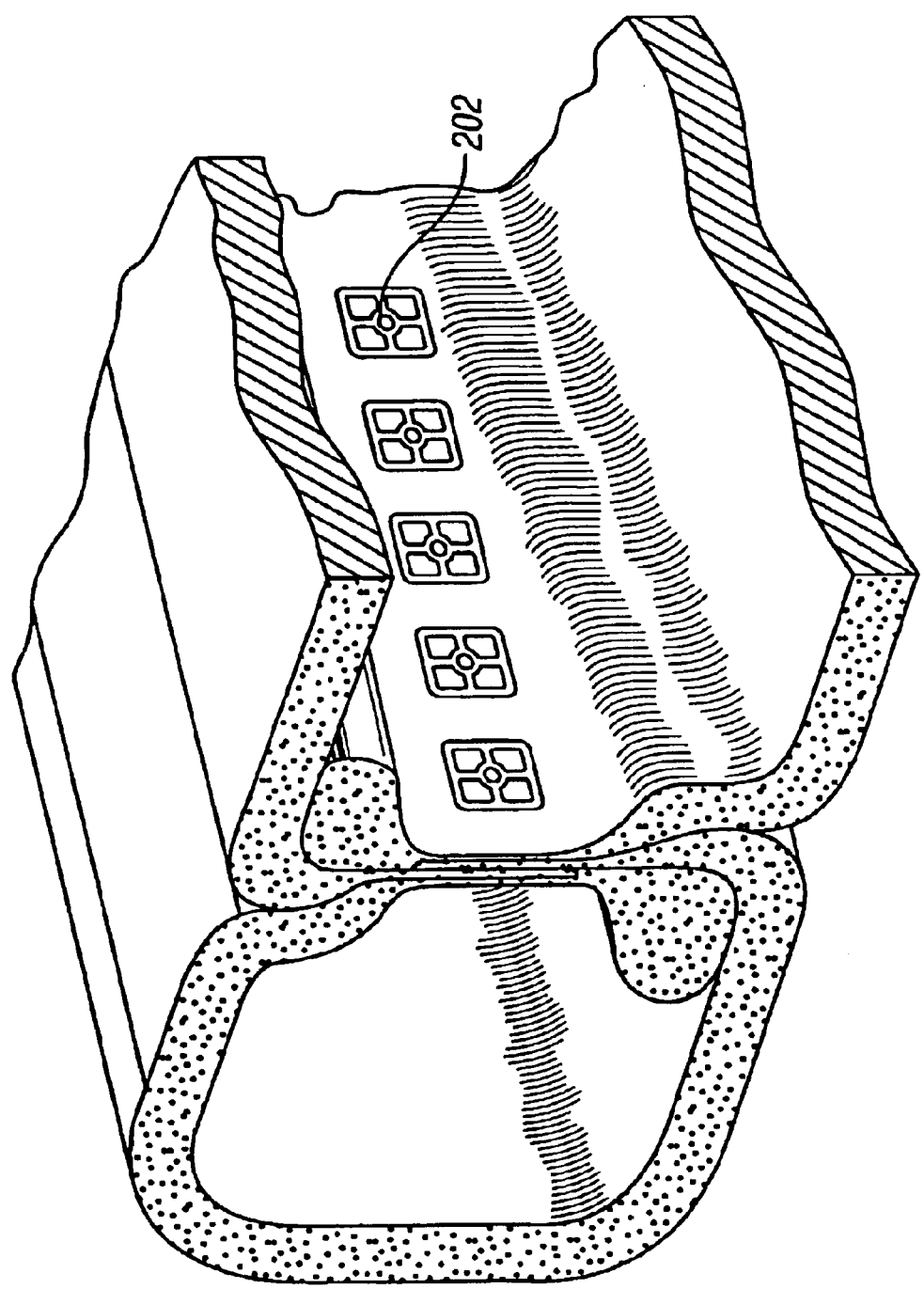

FIGS. 20A and 20B represent depictions of the final result of tissue fold fixation contemplated by the present invention showing a perspective view of the inside of the restricted organ and the resultant fixation zone, using fastening elements 201 or 202 respectively. Although various embodiments have been disclosed, it is contemplated by this description of the devices used for creating the pouch of the present invention, that the fastening assembly will be a flexible endoscopic stapler and that the fastening elements will be staples, preferably formed of titanium or steel, but it is within the scope of this method to use any of the fastening devices disclosed herein to accomplish the same result.

Method of Hollow Organ Volume Reduction

Figure 8B:
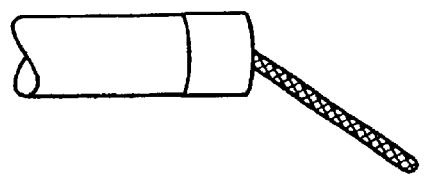
FIGS. 8, 8A, 8B, 9, 9A, 10, 11, 11A and 11B depict an example of sequential procedural steps for performing an organ division or restriction as taught by the present invention. Restriction of the stomach is used for illustrative purposes.
Figure 8A:
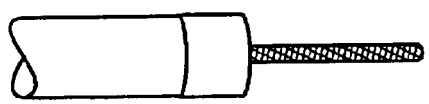
Figure 8:
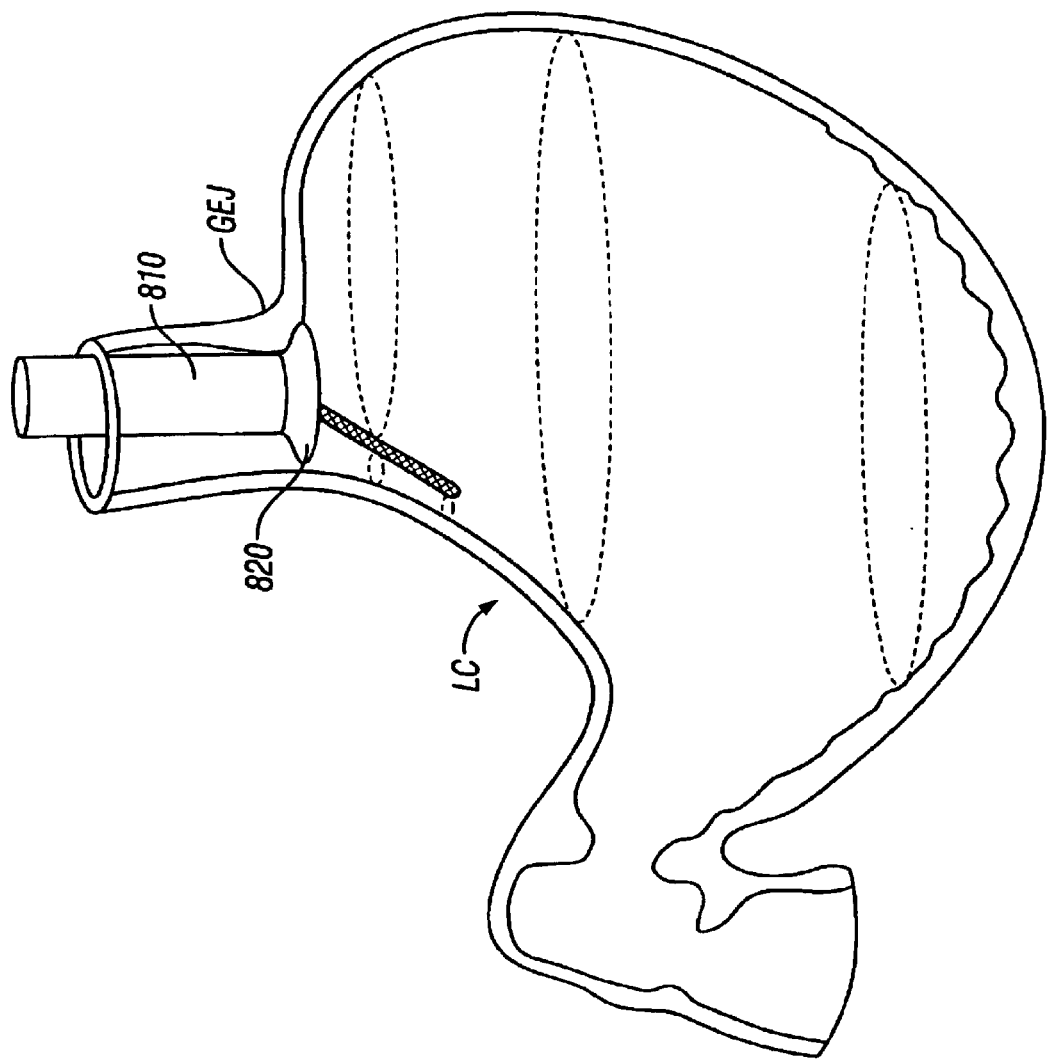

A clinical work-up, including a physical and mental assessment of the patient may be performed to determine whether a transoral stomach reduction clinically indicated. This assessment may include inspecting the esophagus and stomach of the patient to determine whether any contraindications exist for undertaking the procedure such as ulcerations, obstructions, or other conditions that may preclude treatment. Once the procedure has been determined to be appropriate, as depicted in FIG. 8, either in an operating room with the patient under general anesthesia, or in an endoscopy suite with the patient under sedation, the operator can introduce tissue acquisition device 810 down the patient's esophagus and into the stomach to a location just beyond the GE Junction. Once in place, an optional calibration device 820, such as a balloon or bougie can be inflated or deployed to assist in correctly sizing the pouch to be created. The operator may gently pull on the tissue acquisition device 810 until the calibration balloon contacts the GEJ. The operator can determine, by tactile feedback (resistance) as the calibration balloon snugs up against the GEJ and esophagus, where to place the tissue acquisition device to optimally position it longitudinally between the GEJ and the LC. Alternatively, the physician may opt to use direct vision and place an endoscope through the main lumen of the tissue acquisition device to view the site of entry and resultant treatment zone.

Figure 9A:
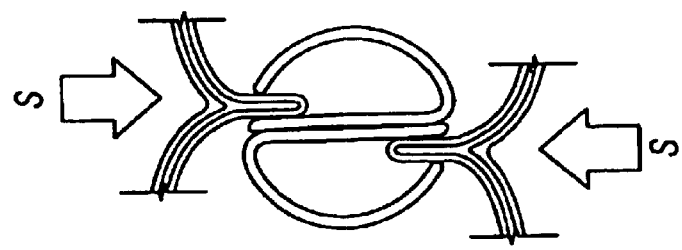
Figure 9:
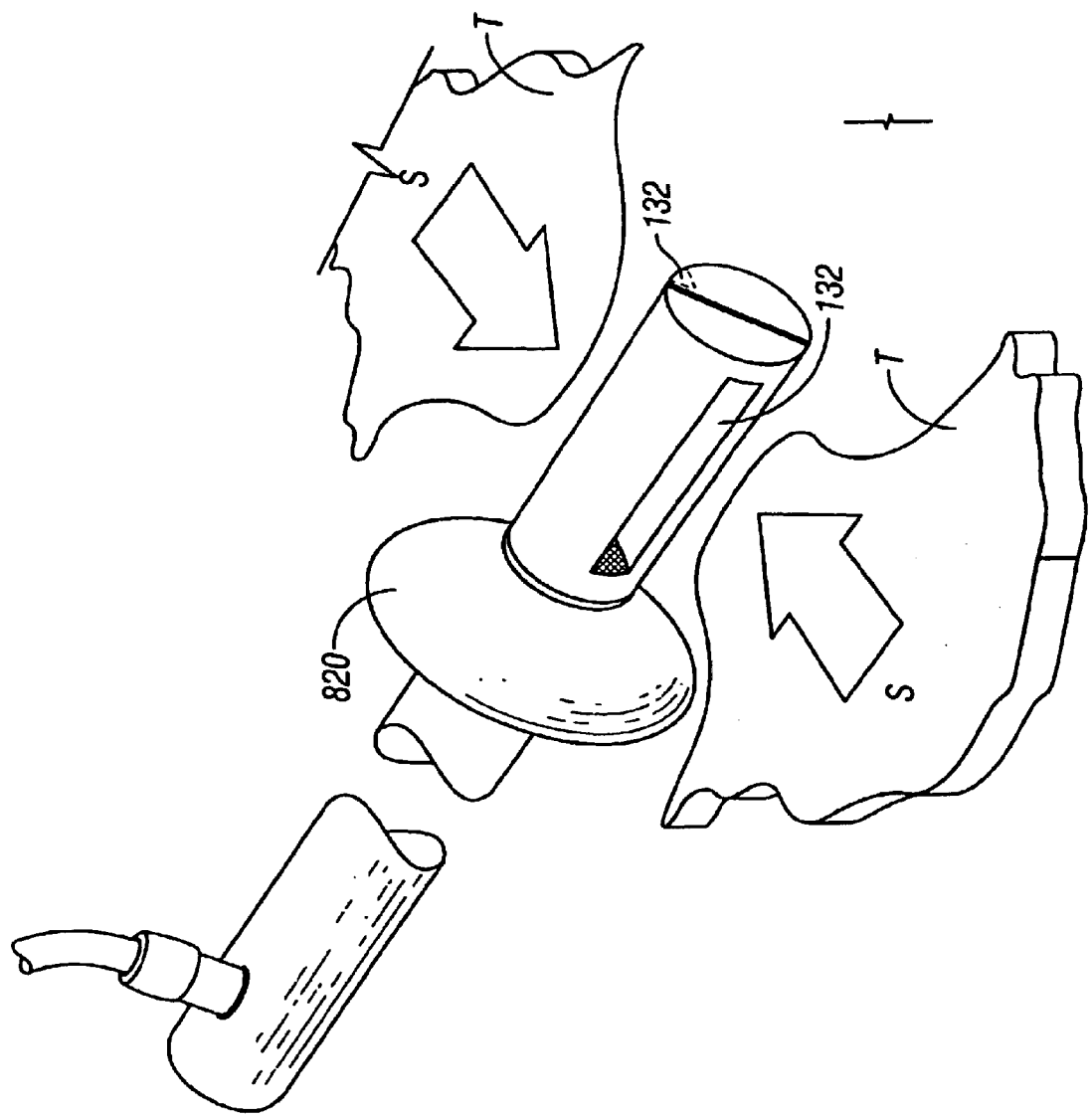
Figure 10:
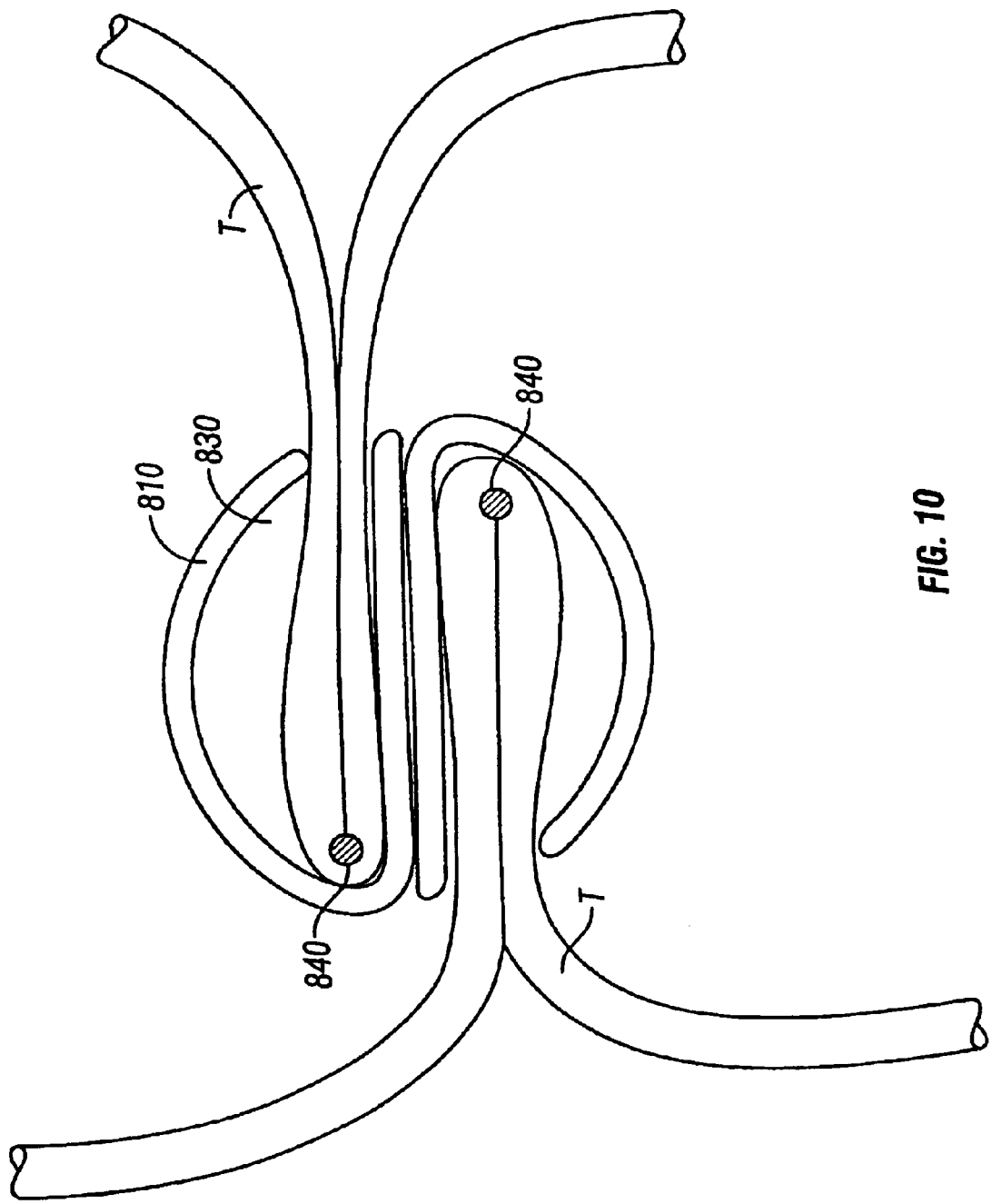

The operator may then orient the tissue acquisition device axially to ensure that the vacuum ports of tissue acquisition device, once activated, will contact the anterior and posterior regions of the stomach thereby acquiring tissue in the appropriate configuration to create the desired pouch or partition. This is done by aligning an indicator emblem (not shown) with, e.g., the patient's nose (patient should be lying on his or her back with nose pointed directly at the ceiling). The endoscope, if still inserted, can be removed and the distal end of the tissue acquisition device can be articulated to approximate the ultimate fixation zone, and locked or otherwise secured in place (See detail in FIGS. 8A and 8B). The operator may then attach a vacuum source similar to the wall suction units found in general operating suites (not shown) to the filler port of the tissue acquisition device, checking to make sure that the vacuum source is delivering approximately 600 mmHg vacuum. The operator may then open the tissue acquisition device stopcock to allow vacuum pressure to develop in the lumens attached to the vacuum ports. As depicted in FIGS. 9 and 9A, tissue folds will begin to invaginate within the vacuum ports 132 and into the main lumen of the tissue acquisition device. Once vacuum pressure has stabilized (i.e. a seal has developed between the device and the tissue), if desired, a mechanical tensioning mechanism of the present invention can be actuated to assist in mechanical tissue acquisition as earlier described. At this point, the operator may want to reinsert the scope to confirm that the tissue folds are equally within the vacuum ports and that the tensioning members are holding the folds consistent with the schematic depiction in FIG. 10. FIG. 10 depicts an end on view of the main lumen of tissue acquisition device 810, including guide posts 840 and vacuum ports 830. Tissue T is approximated and read to be secured by a fastening component of the present invention.

Once this is confirmed, the operator may insert the fastening assembly of the present invention through the main lumen making sure to align the fastening assembly with an indicator on the tissue acquisition device indicating that the jaws of the fastening assembly are passing on either side of the approximated dual folds of tissue within the tissue acquisition device main lumen as previously described and depicted in FIG. 16. The fastening assembly will snap into place with the tissue acquisition device at the correct alignment. As noted previously, to accomplish the correct placement of the jaws around the tissue, the operator may deploy the fastening assembly handle to close the jaws sufficient to pass on either side of the acquired tissue. Once in place, the operator may deploy the fastening assembly handle to clamp the jaws down on the acquired tissue. As referenced earlier, the clamping function, followed by the firing of the fasteners, allows the system to apply sufficient force to the acquired tissue to flatten the tissue to be fastened so that the critical external stomach layers (muscularis and serosa) of both tissue folds are contained within the fixation zone and mucosal tissue is minimized within this zone.

Figure 11A:
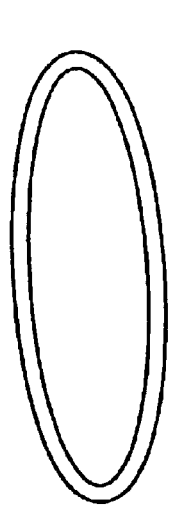
Figure 11B:
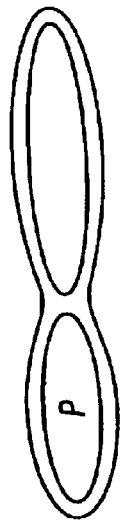
Figure 11:
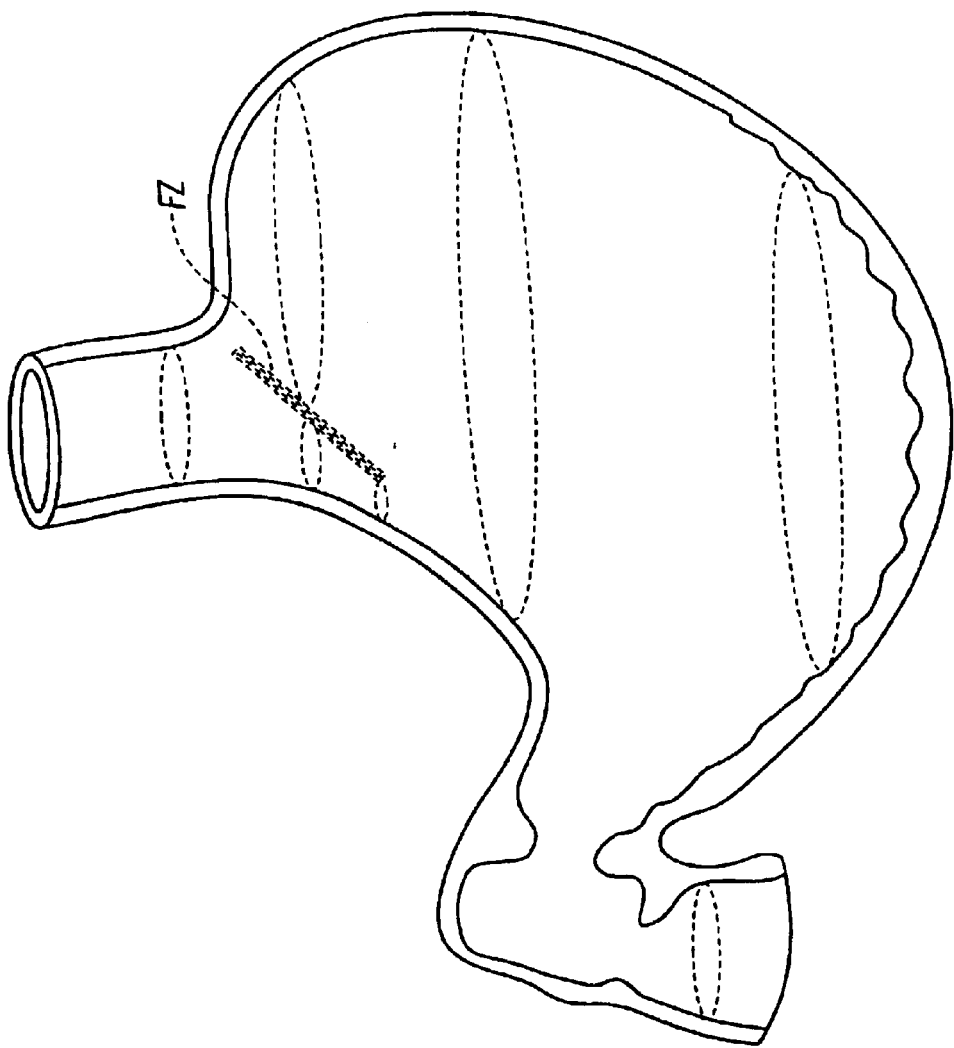

Following the clamping, the operator may then actuate the handle 151 of fastening assembly 150 to deploy fastening elements through the acquired tissue. Once fasteners are deployed, the operator may disengage the actuation mechanism to back off the fastener driver mechanism (not shown). Similarly, the operator may then disengage the clamp jaws of the fastening assembly, unclamping the fastened tissue folds. If utilized, the calibration balloon can then be deflated and the tissue acquisition device and fastening assembly can be withdrawn from the patient. The operator can then redeploy the endoscope to inspect the resultant pouch. The end result of the procedure is schematically depicted in FIG. 11, including a cross section of the stomach prior to reduction (FIG. 11A), a cross section of the stomach post reduction (FIG. 11B) showing pouch lumen P, and an internal view of the fixation zone (FZ) within the greater geometry of the stomach organ (FIG. 11).

The steps of performing the method of the preferred embodiment of organ division or reduction (transoral stomach reduction) are used to illustrate in detail the method of the present invention, however the present invention is not limited thereby. Use of these steps and the tools deployed therein may be varied to achieve a similar result in other hollow body organs and it is anticipated that such techniques can be employed to divide or restrict other hollow body organs such as organs of the gastrointestinal tract such as bowel, stomach or intestine, bladder, uterus, and heart (such as in ventricular reduction or treatment of chronic heart failure). In addition, as previously mentioned, other procedures such as the treatment of GERD may also benefit from the methods and devices disclosed herein. While certain embodiments have been illustrated and described in detail, those having ordinary skill in the art will appreciate that various alternatives, modifications, and equivalents may be used and that the invention is not intended to be limited to the specifics of these embodiments.

We claim:

1. A method of partitioning a hollow body organ from within, said method comprising:

positioning a tissue acquisition device into the hollow body organ, said tissue acquisition device having a proximal end and distal end and a lumen therebetween with a tissue acquiring mechanism at the distal end thereof;

acquiring a first tissue region and a second tissue region within at least one opening defined in said tissue acquiring mechanism such that said acquired tissue is in juxtaposition with each other;

advancing a tissue fastening assembly within the lumen to the juxtaposed tissue, said tissue fastening assembly device having clamping distal portion; and actuating the clamping distal portion to engage said juxtaposed tissue with a fastening element such that said juxtaposed tissue remain affixed to one another.

2. The method of claim 1 wherein positioning the tissue acquisition device comprises transorally advancing the tissue acquisition device into the hollow body organ.

3. The method of claim 1 wherein acquiring the first tissue region and the second tissue region comprises drawing the tissue within the opening via a vacuum force.

4. The method of claim 1 further comprising translationally moving the first tissue region and the second tissue relative to each other from a first configuration to a second configuration in which the tissue regions are positioned into apposition with each other prior to actuating the clamping distal portion.

5. The method of claim 4 further comprising tensioning the juxtaposed tissue while translationally moving the first tissue region and the second tissue region.

6. The method of claim 4 wherein the tissue acquiring mechanism comprises at least one fenestration defined along the tissue acquiring mechanism.

7. The method of claim 1 wherein advancing the tissue fastening assembly comprises advancing a stapler to the juxtaposed tissue.

8. The method of claim 1 wherein actuating the clamping distal position comprises engaging the juxtaposed tissue to create a tissue bridge such that a pouch is created within the hollow body organ.

9. The method of claim 8 wherein the tissue bridge is angled relative to an interior wall of the hollow body organ such that a narrow channel is maintained in communication between the pouch and the hollow body organ.

10. The method of claim 8 further comprising engaging tissue folds in multiple areas within the hollow body organ.

11. The method of claim 1 wherein the first tissue region comprises a posterior wall of the hollow body organ and the second tissue region comprises the anterior wall of the of hollow body organ.

12. The method of claim 1 wherein the fastening element is selected from the group consisting of staples, clamps, and rivets.

13. The method of claim 9 wherein the fastening element is bioabsorbable or biofragmentable.

14. A method of partitioning a hollow body organ from within, said method comprising:

positioning a tissue acquisition device into the hollow body organ, said tissue acquisition device having a proximal end and a distal end and a lumen therebetween with a tissue acquiring mechanism at the distal end thereof;

acquiring a first tissue region within at least one opening defined in said tissue acquiring mechanism such that said first tissue region acquires a partitioning configuration;

advancing a tissue fastening assembly within the lumen to the first tissue region said tissue fastening assembly device having a clamping distal portion;

actuating the clamping distal portion to engage said first tissue region with a fastening element such that said first tissue region within remains affixed in the partitioning configuration; and acquiring a second tissue region within the at least one opening such that the second tissue region is in juxtaposition with the first tissue region prior to actuating the clamping distal portion.

15. The method of claim 14 further comprising tensioning the juxtaposed tissue while translationally moving the first tissue region and the second tissue region.

* * * * *

UNITED STATES PATENT AND TRADEMARK OFFICE
CERTIFICATE OF CORRECTION

PATENT NO. : 6,773,440 B2
DATED : August 10, 2004
INVENTOR(S) : Jamy Gannoe et al.

It is certified that error appears in the above-identified patent and that said Letters Patent is hereby corrected as shown below:

Column 12,
Line 40, delete "claim 4" and insert -- claim 1 --.
Line 59, delete "of the of" and insert -- of the --.

Signed and Sealed this

Fifth Day of April, 2005

JON W. DUDAS
*Director of the United States Patent and Trademark Office*